(12) United States Patent
Madura

(10) Patent No.: US 7,811,803 B2
(45) Date of Patent: *Oct. 12, 2010

(54) METHODS AND COMPOSITIONS FOR RAPID PURIFICATION OF PROTEASOMES AND METHODS OF USE OF COMPONENTS THEREOF

(75) Inventor: Kiran Madura, Bridgewater, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 556 days.

This patent is subject to a terminal disclaimer.

(21) Appl. No.: 11/442,840

(22) Filed: May 30, 2006

(65) Prior Publication Data

US 2006/0281118 A1 Dec. 14, 2006

Related U.S. Application Data

(63) Continuation-in-part of application No. 09/918,036, filed on Jul. 30, 2001, now abandoned, which is a continuation of application No. 09/100,802, filed on Jun. 19, 1998, now Pat. No. 6,294,363.

(60) Provisional application No. 60/050,171, filed on Jun. 19, 1997.

(51) Int. Cl.
*C12N 9/64* (2006.01)
(52) U.S. Cl. .......................... 435/226; 630/415; 630/417
(58) Field of Classification Search ........................ None
See application file for complete search history.

(56) References Cited

U.S. PATENT DOCUMENTS 5,132,213 A 7/1992 Bachmair et al.

OTHER PUBLICATIONS

Baboshina et al, Novel Multiubiquitin chain linkages catalyzed by the conjugating enzymes E2epf and Rad6 are recognized by 26 S proteosome subunit 5, J. Biol. Chem, 1996, 271:2823-2831.
Biggins, S., I. Ivanovska, and M.D. Rose. Yeast Ubiquitin-like Genes Are Involved in Duplication of the Microtubule Organizing Center. *The Journal of Cell Biology*. 1996. 133-1331-1346.
Ciechanover, A. The Ubiquitin -Proteasome Proteolytic Pathway. *Cell*. 1994. 79:13-21.
Coux, O., K. Tanaka, and A.L. Goldberg. Structure and Functions of the 20S and 26S Proteasomes. *Annu. Rev. Biochem*. 1996. 65:801-847.
Deveraux et al, A 26 Sprotease subunit that binds ubiquitin conjugates, J. Biol. Chem. 1994, 269:7059-7061.
Fu et al, Multiubiquitin chain binding and protein degradation are mediated by distinct domains within the 26 S proteasome subunit Mcb1, J. Biol. Chem 1998, 23: 1970-1981.
Garrett, K.P., T. Aso, J.N. Bradsher, S.I. Foundling, W.S. Lane, R.C. Conaway, and J.W. Conaway. Positive Regulation of General Transcription Factor SIII by a Tailed Ubiquitin Homolog. *Proc. Natl. Acad. Sci. USA*. 1995 92:7172-7176.
Glotzer, M., Murray, A.W., and Kirschner, M.W. Cyclin is Degraded by the Ubiquitin Pathway. *Nature*. 1991. 349:132-138. USA.
Harakas, Biospecific Affinity Chromatography, Protein Puriffication Process Engineering, Harrison ed., Marcel Dekker, Inc. New York, 1994, pp. 259-316.
Hershko, A. The Ubiquitin Pathway for Protein Degredation. *Trends in Biochem. Sci.* 1996. 84:277-287.
Hochstrasser, M. Ubiquitin-Dependent Protein Degradation. *Annu. Rev. Genet*. 1996. 30:405-439.
Johnson, E.S., P.C.M. Ma, I.M. Ota, and A. Varshaysky. A Proteolytic Pathway That Recognizes Ubiquitin as a Degradation Signal. *the Journal of Biological Chemistry*. 1995. 270:17442-17456.
Johnson, E.S., B. Bartel, W. Seufert, and A. Varshaysky. Ubiquitin as a Degradation Signal. *The EMBO Journal*. 1992. 11:497-505.
Madura et al, Degradation of Galpha by the N-end rule pathway, Science, 1994, 265:1454-1457.
Mahajan, R., C. Delphin, T. Guan, L. Gerace, and F. Melchior. A Small Ubiquitin-Related Polypeptide Involved in Targeting RanGAP1 to Nuclear Pore Complex Protein RanBP2. *Cell*. 1997. 88:97-107.
Mannen et al, Cloning and expression of human homolog HSMT3 to yeast SMT3 suppressor of MIF2 mutations in a centromere protein gene, Biochem. Biophys. Res. commun. 1996, 222:178-180.
Masutani et al, Purification and cloning of a nucleotide excission repair complex involving the xeroderma pigmentosum group C protein and a human homologue of yeast RAD23, EMBO J. 1994, 13:1831-1843.
Ortolan et al, The DNA repair protein Rad23 is a negative regulator of multi-ubiquitin chain assembly, Nature Cell Biol. 2000, 2:601-607.
Peters, J.M., Harris, J.R., Kleinschmidt, J.A. Ultrastructure of the ~ 26S Complex Containing the ~ 20S Cylinder Particle (Multicatalytic Proteinase/Proteasome). *European Journal of Cell Biology*. 1991. 56:422-432. USA.
Pickart, C.M. Targeting of Substrates to the 26S Proteasome. *FASEB*. 1997. 11:1055-1066.
Scheffner, M., U. Nuber, and J.M. Huibregtse. Protein Ubiquitination Involving an E1-E2-E3 Enzyme Ubiquitin Thioester Cascade. *Nature*. 1995. 373:81-83.
Schrauber et al. Rad23 links DNA repair to the ubiquitin/proteasome pathway, Nature, 1998, 391; 715-718.
Thrower et al, Recognition of the ubiquinin proteolitic sygnal, EMBO J. 2000, 19:94-102.
Tongaonkar et al, Reconstruction ubiquitination reaction with affinity purified components and 32-ubiquitin, Analyt. Biochem. 1998, 260: 235-141.
Tongaonkar et al., Evidence for an iteraction between ubiquitin-conjugating enzymes and the 26S proteosome, Mol. Cell. Biol. 2000, 20:4691-4698.
Udvardy, Purification and characterization of a multiprotein component of the Drosophila 26 S (1500 kD) proteolytic complex, J. Biol. Chem. 1993, 12: 9055-9062.

(Continued)

*Primary Examiner*—Rebecca E. Prouty
(74) *Attorney, Agent, or Firm*—Licata & Tyrrell, P.C.

(57) ABSTRACT

Disclosed are methods for rapidly and efficiently purifying proteasomes using fusion proteins having homology to ubiquitin. Also disclosed are methods for assessing aberrant cell growth utilizing fusion proteins have homology to ubiquitin and a signal producing moiety.

6 Claims, 21 Drawing Sheets

OTHER PUBLICATIONS

Van Der Spek, P.J., C.E. Visser, F. Hanaoka, B. Smit, A. Hagemeuer, D. Bootsma, and J.H.J. Hoeumakers. Cloning, Comparative Mapping, and RNA Expression of the Mouse Homologues of the *Saccharomyces cervisiae* Nucleotide Excision Repair Gene *RAD23*. *Genomics*. 1996. 31:20-27.

Van Nocker, S., Deveraux, Q., Rechsteiner, M., Vierstra, R.D.. Arabiodopsis MBP1 Gene Encodes a Conserved Ubiquitin Recognition Component of the 26S Proteasome. *Proc. Natl. Acad. Sci.*. 1996. 93:856-860. Biochemistry. USA.

Varshaysky, A. The Ubiquitin System. *Trends Biochem. Sci..* 1997. 22:383-387.

Watkins, J.F., P. Sung, L. Prakash, and S. Prakash. The *Saccharomyces cerevisiae* DNA Repair Gene *RAD23* Encodes a Nuclear Protein Containing a Ubiquitin-Like Domain Required for Biological Function. *Mollecular and Cellular Biology*. 1993. 13:7757-7765.

Wilek et al., The purification of biologically active compounds by affinity chromatography, Methods in Biochemical Analysis, 1976, 23:347-385.

Tanaka, K., "Breakthroughs and Views—Molecular Biology of the Proteasome", Biochem. Biophys. Res. Commun., 1998, 247:537-541.

Baker, R. et al., "The Yeast Homolog of Mammalian Ribosomal Protein S30 Is Expressed from a Duplicated Gene Without a Ubitiquin-like Protein Fusion Sequence", J. Biol. Chem., 1996, 271:13549-13555.

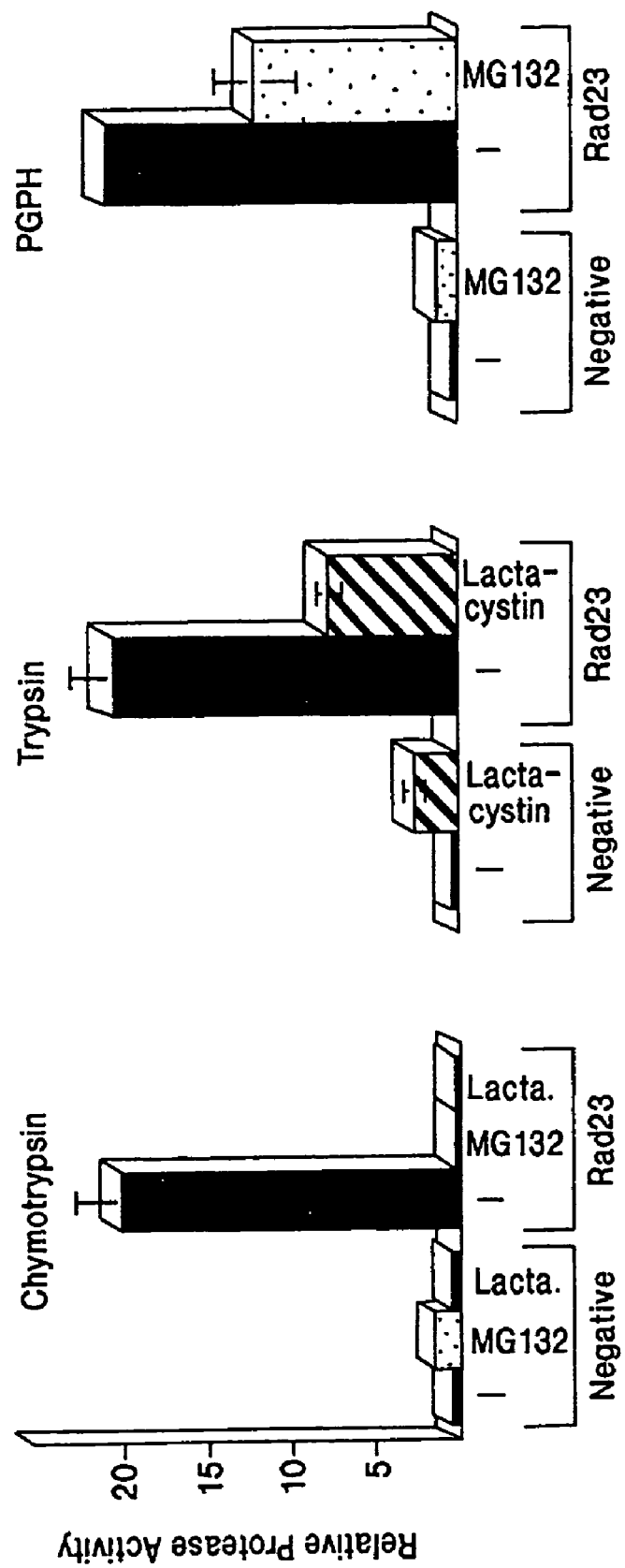

Vector

P$_{GAL}$::
RAD23 rad23∆

0  10  30  60 ubc4Δ
ubc5Δ ubc2Δ ubr1Δ pol II<sup>ts</sup> (37°C)

hydroxy-urea

α-factor

Rad23-ha     $^{\Delta ub}$Rad23-ha logarithmic growth     stationary phase 0  10  30  60 pre1-1
pre2-2 cim5-1 doa4Δ-1 mcb1Δ pep4Δ
prb1Δ

```
IRT1 602 VHWDDIAGLESAKYSLKEAVVYPFLRPDLFRGL..REPVRGMLLFGPPGTGKTMLARAVA
YTA6 172 VIWEDIAGLRNAKNSLKEAVVYPFLRPDLFKGL..REPVRGMLLFGPPGTGKTMIAKAVA
CIM3 206 VTYSDVGGCKDQIEKLREVELPLSPERFATLGIDPPKGILLYGPPGTGKTLCARAVA
CIM5 145 STYDMVGGLTKQIKEIKEVIELPVKHPELFESLGIAQPKGVILYGPPGTGKTLLARAVA

IRT1 660 TESHSTFFSISASSITSKYLGESEKLVRALFAIAKKLSPSIIFVDEIDSIMGSRNNENE
YTA6 230 TESNSTFFSVSASSLLSKYLGESEKLVRALFYMAKKLSPSIIFIDEIDSMLTAR.SDNE
CIM3 265 NRTDATFIRVIGSELVQKYVGEGARMVRELFEMARTKKACIIFFDEIDAVGGARFDDGA
CIM5 204 HHTDCKFIRVSGAELVQKYIGEGSRMVRELFVMAREHAPSIIFMDEIDSIGSLRVEGSG

IRT1 719 NESS...RRIKNEFLVQWSSLSSAARGSNKSNTNNSDTNGDEDDTRVLVLAATNLPWSID
YTA6 288 NESS...RRIKTELLIQWSSLSSLSSATAQSEDRN......NTLDSRVLVLGATNLPWAID
CIM3 324 GGDNEVQRTMLELITQLDGF......DPRGNIKVWFATNRPNTLD
CIM5 263 GGDSEVQRTMLELLNQLDGF......ETSKNIKIIMATNRLDILD

IRT1 776 ERAARR..RFVRRQYIPLPEDQTRHVQFKKTISHQKHTLTESDFFDETVKITEGYSGSDIL
YTA6 337 DAARR..RFSRKLYIPLPDYETRLYELKRLMAKQKTSLQDLDYELITEMTEGFSGSDLL
CIM3 363 PALLRPGRIDRKVEFSLPDLEGR.ANIFRIHSRKMNLTRGINLRKVAEKMNGCSGAELR
CIM5 302 PALLRPGRIDRKIEFPPPSVAAR.AEIILRIHSRKMNLTRGINLRKVAEKMNGCSGADVK

IRT1 833 SLAKDAAMGPLRDLGDKL
YTA6 394 SLAKEAAMEPIRDLGDKL
CIM3 421 SVCTEAGMFAIRARRKVA
CIM5 360 GVCTEAGMYALRERRIEV
```

FIG. 12A

```
Ub       --MQIFVKTLTGKTITLE--VEPSDTIENVKAKIQDKEG----IPPDQQRLIFAGKQLEDG  53
RUB1     --MIVKVKTLTGKEISVE--LKESDLVYHIKELLEEKEG----IPPSQQRLIFQGKHSDDK  53
HHR23-B  --MQVTLKTLQQQTFKID--IDPEETVKALKEKIESEKGKDAFPVAGQKLIYAGKILNDD  56
HHR23-A  MAVTITLKTLQQQTFKIR--MEPDETVKVLKEKIEAEKGRDAFPVAGKLIYAGKILSDD  58
DSK      MSLNIHIKS-GQDKWEVN--VAPESTVLQFKEAINKANG----IPVANQRLIYSGKILKDD  54
RAD      -MVSLTFKNFKKEKVPLD--LEPSNTILETKTKLAQSIS----CEESQIKLIYSGKVLQDS  54
212      -AVHLTLKKIQAPKFSIEHDFSPSDTILQIKQHLISEEK--ASHISEIKLLLKGKVLHDN  57
                                            K          (SEQ ID NO:1)  XLXXXGKXXXD
                                                                      K

Ub       RTLSDYNIQKESTLHLVLRLRGG----  76
RUB1     LTVTDAHLVEGMQLKLVLTLRGG----  76
HHR23-B  TALKEYKIDEKNFVVVMVTKPKA----  79
HHR23-A  VPIRDYRIDEKNFVVVMVTKTKA----  81
DSK      QTVESYHIQDGHSVHLVKSQPKP----  77
RAD      KTVSECGLKDGDQVVFMVSQKKS----  77
212      LFLSDLKVTPANSTITVMIKPNPTIS  83
```

FIG. 19A

```
SMT3B   MAD-----EKPKE-----GVKTENN---DHINLKVAGQDGSVVQFKIKRHTPLSKLMKAYCE  49
SMT3A   MSE-----EKPKE-----GVKTEN----DHINLKVAGQDGSVVQFKIKRHTSLSKLMKAYCE  48
SUMO1   MSD-----QEAKPSTEDLGDKKEG---EYIKLKVIGQDSSEIHFKVKMTTHLKKLKESYCQ  53
SMT3    MSDSEVNQEAKP------EVKPEVKPETHINLKVS-DGSSEIFFKIKKTTPLRRLMEAFAK  54
                                                                  XXXXX
                                        K  K
SMT3B   RQGLSMRQIRFRFDGQPINETDTPAQLEMEDEDTIDVFQQQTGGVY--  95
SMT3A   RQGLSMRQIRFRFDGQPINETDTPAQLRMEDEDTIDVFQQQTGGVPE-  95
SUMO1   RQGVPMNSLRFLFEGQRIADNHTPKELGMEEEDVIEVYQEQTGGHSTV 101
SMT3    RQGKEMDSLRFLYDGIRIQADQTPEDLDMEDNDIIEAHREQIGGAT-- 100
        RQG (SEQ ID NO:2)
```

FIG. 19B

METHODS AND COMPOSITIONS FOR RAPID PURIFICATION OF PROTEASOMES AND METHODS OF USE OF COMPONENTS THEREOF

INTRODUCTION

This application is a continuation-in-part application of U.S. Ser. No. 09/918,036, filed Jul. 30, 2001, now abandoned, which is a continuation application of U.S. Ser. No. 09/100,802 filed Jun. 19, 1998, now issued as U.S. Pat. No. 6,294,363, which claims the benefit of priority from U.S. Provisional Application Ser. No. 60/050,171, filed Jun. 19, 1997, the contents of which are incorporated herein by reference.

This invention was made in the course of research sponsored by the National Institutes of Health (NIH Grant No. GM-52058). The U.S. government may have certain rights in this invention.

BACKGROUND OF THE INVENTION

The degradation of cellular proteins is necessary for the biological well-being of all organisms. Regulators of cell growth and development, and components of the immune and cellular defense mechanisms are regulated by proteolysis. Membrane receptors and transcription factors activated by cytokines, such as interleukins and interferons, are regulated by protein degradation.

The major pathway of intracellular proteolysis involves the ubiquitin/proteasome system. Ubiquitin, a 76 amino acid polypeptide, is the most highly conserved protein in eukaryotic evolution. There are only three amino acid differences between yeast and human ubiquitins. Extensive studies during the past decade have shown that the covalent attachment of ubiquitin to cellular proteins marks them for destruction. Substrates that are linked to ubiquitin are degraded by a multicatalytic protease called the proteasome. During the past few years many targets of the ubiquitin/proteasome system have been discovered and remarkably they include a broad range of regulators of cell growth. Some of the proteins destroyed by the ubiquitin/proteasome system include cyclins, cyclin-dependent kinases (CDK's), NFκB, IκBα, cystic fibrosis transduction receptor, p53, ornithine decarboxylase (ODC), 7-membrane spanning receptors, Cdc25 (phosphotyrosine phosphatase), Rb, Gα, c-Jun and c-Fos.

The ubiquitin/proteasome pathway is also essential for the stress-response and for the generation of antigenic peptides in MHC Class I molecules. It is clear that defects in the functioning of the ubiquitin/proteasome system can have severe consequences on biological homeostasis. Indeed, mutations that affect the degradation of many of the proteins listed above have been associated with tumorigenesis.

The 26S-proteasome comprises two distinct sub-complexes. The core complex has a sedimentation velocity of 20S and contains a variety of degradative activities. The 20S core is highly conserved across evolutionary distance and consists of a barrel of 4 rings. Each ring contains 7 subunits of either α class or β class. The rings are oriented so that two α-subunit-containing rings are on the outside, while two β-subunit containing rings are juxtaposed on the inside. Thus, the 20S core is identical at its two ends. The x-ray structure of the archaebacterial proteasome has recently been resolved and was shown to contain a narrow pore in each α ring, and a large central cavity formed by the β rings. Accordingly, the central cavity is not exposed to the cellular environment, thereby preventing non-specific degradation of cellular proteins. Proteins targeted for degradation are first threaded through the narrow pores in the α rings before they gain access to the central catalytic cavity.

The second sub-complex, referred to as the 19S-regulatory complex, binds to the ends of the 20S core and regulates access of cellular proteins to the catalytic cavity. The 19S complex, together with the 20S core, make up the 26S-proteasome. The 19S complex has at least 6 distinct ATPase subunits for promoting unfolding of proteolytic substrates so that they can be channeled through the narrow pores of the 20S core. The 19S complex contains as many as 20 subunits, which include a multiubiquitin-chain binding protein, isopeptidases and at least 6 ATPases.

The Rad23 gene of *Saccharomyces cerevisiae* is necessary for efficient nucleotide excision repair of damaged DNA. In vitro studies indicate that this factor may play a role in assisting the assembly of the repair complex at the site of damage. Accordingly, interactions between Rad23p and other repair proteins including Rad4p, Rad14p, and subunits of TFIIH have been proposed. Thus far, however, the exact biochemical function of Rad23p in DNA repair has remained unclear.

Rad23p has an $NH_2$-terminal domain with striking homology to ubiquitin (22% identity, 43% homology). It has been shown that this ubiquitin-like domain is required for repair activity of the protein and that the domain can be replaced by the sequence of wild-type ubiquitin (Watkins, et al. (1993) *Mol. Cell. Biol.* 13:7757-7765). In addition, a family of proteins with similar ubiquitin-like domains have been discovered. Unfortunately, these family members have diverse species of origin and apparently disparate functions and thus have provided no clue as the exact role of this domain.

As noted above, impaired activity of the proteasome is implicated in many diseases in humans. This observation has stimulated considerable research activity in the identification of novel therapeutic agents for inhibiting and/or stimulating the activity of the proteasome. These studies have been hindered by the inefficient, time-consuming, biochemical protocols available for the purification of proteasomes. The present invention describes a rapid and efficient proteasome purification method and provides novel methods of use of various proteasome subunits so purified.

SUMMARY OF THE INVENTION

The present invention provides compositions and a rapid and efficient method for the purification of proteasome complexes from a variety of cell types. In accordance with the present invention, it has been discovered that the ubiquitin-like N-terminal domain of a yeast protein, Rad23, has high affinity for the proteasome. Accordingly, this domain or homologues thereof can be immobilized to a suitable solid support and used to isolate the proteasome from cell lysates. Following removal of non-specifically bound proteins, the proteasomes are eluted. This method facilitates the molecular characterization the proteasome. Ubiquitin-like domains (UbL) in cellular proteins vary slightly between species. In one embodiment of the invention, UbL-domains from a given species is used for proteasome purification from cell lysates derived from cells of that species.

Another aspect of the invention is a kit of materials useful in performing the proteasome purification method of the invention. A kit according to this aspect of the invention contains a solid support to which a UbL of interest has been affixed as well as suitable buffers for eluting proteasome preparations.

In a further embodiment of the invention, it has been discovered that this same N-terminal ubiquitin-like domain of Rad23, UbL$^{R23}$, functions as a degradation signal in actively growing cells. Fusion proteins containing this domain are provided herein. Reporter proteins attached to the UbL domain (UbL$^{R23}$-reporter) are rapidly degraded in logarithmically growing cells. Since a primary feature of malignant cells is the aberrant rate of cell growth, the UbL$^{R23}$-reporter provides a powerful way to assess the proliferative potential of tumor cells. In yet another embodiment of the invention, the efficacy of anti-cancer drugs can be assessed by determining the stability of the UbL$^{R23}$-reporter fusion proteins.

In a further aspect of the invention, compositions and methods are provided for enhancing the thermostability of fusion proteins containing the UbL domain. Such fusion proteins can be used to advantage in chemical reactions requiring thermostable reagents, such as the polymerase chain reaction (PCR). In this embodiment of the invention, DNA constructs are generated wherein a DNA sequence encoding a UbL-domain is operably linked to a DNA sequence encoding the protein to be thermostabilized using standard molecular biological techniques. Following expression of the DNA construct in a suitable host cell, the thermostable fusion protein is purified and utilized in biochemical assays requiring high temperatures.

In summary, the methods and kits of the invention are particularly useful for the assessing proteolytic degradation of cellular components via the proteasome. The DNA constructs of the invention encoding fusion proteins containing UbL domains are useful for assessing the proliferative potential of malignant cells. UbL domains can also be utilized to enhance the thermostability of fusion proteins.

BRIEF DESCRIPTION OF THE DRAWINGS

FIG. 1A depicts the positions of [$^{35}$S] GST fusion proteins and [$^{35}$S] Rad-HA. Yeast strains simultaneously expressing the Rad4-HA and each of the GST-fusion proteins were metabolically labeled with $^{35}$S-methionine for 10 minutes. Extracts were prepared and adsorbed to glutathione-SEPHAROSE. Beads were washed extensively and bound proteins resolved by SDS-PAGE and detected by fluorography. FIGS. 1A, 1B and 1C: Lane 1, GST; lane 2; GST-Rad23; lane 3 GST-$^{\Delta UbL}$-RAd23 and lane 4, GST-UbL$^{R23}$. Rad4-HA is detected in lanes 2 and 3 indicating that it interacts with C-terminal sequences in Rad23. Non-specific interactions of other cellular proteins with GST-UbL$^{R23}$ are indicated by asterisks. FIG. 1B is an immunoblot showing that Cim5 and Cim3 interact with GST-Rad23 and GST-UbL$^{R23}$. FIG. 1C shows that the complex that interacts with GST-Rad23 and GST-UbL$^{R23}$ contains the 20S subunit Pup1-HA. The additional band (asterisk) may represent a precursor form of Pup1-HA. FIG. 1D is a blot showing that native Rad23 can be precipitated on FLAG-agarose beads in extracts derived from a yeast strain expressing Pre1-FLAG, an epitope tagged derivative of a 20S β-subunit. FIGS. 1D and 1E: lane 1, extract from Pre1-flag cells; lane 2 extracts from negative control extract lacking Pre-1-FLAG. FIG. 1E is a blot showing that extracts containing FLAG-Rad23 can specifically precipitate Cim3 and Cim5 on FLAG-agarose beads. These subunits were not recovered from extracts containing a control vector lacking FLAG-Rad23 (lane 2).

FIG. 2 shows a series of graphs depicting the proteolytic activity associated with UbL$^{R23}$. FLAG-Rad23 was immunopurified and incubated with peptide substrates. A control reaction with a strain expressing an unrelated protein is also shown (Negative). The relative levels of chymotrypsin, trypsin and PGPH (peptidylglutamyl-peptide hydrolase)-like activities, and the effect of proteasome inhibitors MG132 and lactacystin are shown. A (−) symbol indicates the absence of the inhibitor. The values represent the average of three measurements.

FIG. 3 is fractionation data showing that GST-R23, Rad4-HA and Cim5 are components of a high molecular weight complex. FIGS. 3A, 3B, and 3C show western blots treated sequentially with antibodies against HA (FIG. 3A), Cim5 (FIG. 3B) and Rad23 (FIG. 3C).

FIG. 5A shows that toxicity in yeast is caused by overexpressing the N-end rule pathway (CSY13, top). This toxicity is suppressed by high levels of RAD23 (CSY41, left), or in rad23Δ (CSY41, right). Isogenic yeast strains were grown in minimal medium containing galactose and lacking appropriate nutrients to maintain plasmids. FIG. 5B is a graph showing that Rad23-HA can complement rad23Δ. Exponential-phase yeast cells (JD47-13C; RAD23, closed squares, CSY85; rad23Δ, closed circles, and CSY131; CSY85 expressing Rad23-HA, open circles) were exposed to 15, 45 and 90 J/m$^2$ UV light (n=3).

FIG. 7A shows Rad23-HA stability in logarithmic- and stationary-phases of growth. The numbers at the top indicate minutes in chase medium. Rad23-HA (arrow) and a SEPHAROSE-interacting yeast protein (*) are indicated in this and subsequent figures. FIG. 7B shows stationary-phase yeast cells labeled for 20 minutes with extracts subsequently prepared to monitor the abundance of $^{35}$S-Rad23-HA. The numbers at the top refer to samples withdrawn during the labeling (in minutes), and those indicated as + refer to minutes in chase medium lacking $^{35}$S-label. Total $^{35}$S-protein was also resolved on a second gel to follow the levels of other cellular proteins. FIG. 7C shows the stability of Rad23$^{1-369}$ is shown in logarithmic- and stationary-phase cells. This C-terminal truncated allele does not possess a HA epitope but displays growth-stage specific degradation similar to Rad23-HA (FIG. 6A above) and UbL$^{R23}$-LacZ (FIG. 9B). FIG. 7D shows that the degradation of other substrates of the ubiquitin system are unaffected by growth conditions. (R-β-gal is a substrate of the N-end rule pathway while ubiquitin-proline-β-gal is a substrate for the ubiquitin-fusion degradation (UFD) pathway. Met-β-gal is not a substrate of either pathway and therefore is stable in both logarithmic and stationary phase cells.

FIG. 8A demonstrates that RYB 262 contains a temperature-sensitive allele of RNA polymerase II. The growth of RY262 expressing Rad23-HA was arrested at 37° C. and pulse-chase analysis was performed. FIG. 8B, hydroxyurea was added to exponentially growing cells (JD47-13C) expressing Rad23-HL and incubated for 2 hours at 30° C. Pulse-chase analysis was carried out when approximately 75% of the cells had arrested growth. FIG. 8C, a bar1-1 strain expressing Rad23-HA was exposed to 10 ng/ml α-factor, and pulse-chase analysis was performed when approximately 95% of the cells had arrested in $G_1$.

FIG. 9A, $^{\Delta UbL}$Rad23-HA was expressed in JD47-13C and stability was compared to Rad23-HA in exponential phase. FIG. 9B, $UbL^{R23}$ was linked to β-galactosidase and the stability of $UbL^{R23}$-LacZ was determined in JD47-13C. A cluster of protein bands corresponding to $UbL^{R23}$-LacZ was detected in stationary-phase extracts and are indicated by the bracket. $UbL^{R23}$-LacZ was almost undetectable in exponential-stage cells.

FIG. 11A, pre1-1/pre2-2; FIG. 11B, Cim5; FIG. 11C, doaΔ-1; FIG. 11D. mcb1Δ; FIG. 11E, pep4Δprb1Δ. An arrow indicates the position of Rad23-HA. A protein of approximately 70 kD which binds SEPHAROSE non-specifically is indicated by the asterisks.

FIGS. 12A and 12B are a sequence alignment and graph showing that Rad23 interacts with a subunit of the 26S proteasome. Rad23p was linked to lexA and Irt1 was isolated in a 2-hybrid experiment. FIG. 12A shows the amino acid sequence corresponding to the ATPase domain of Irt1 is aligned with the sequence of closely related homologs of 26S proteasome subunits. FIG. 12B is a graph showing that the interaction between Rad23 and Irt1, and three C-terminal truncated alleles of Irt1, as determined by measuring β-galactosidase activity in the 2-hybrid yeast strain harboring both plasmids. The data are representative of 6 independent measurements and are indicated in Miller units.

FIG. 13A: Lane 1 contains a GST control, and lanes 2-6 contain GST linked to $UbL^{R23}$, Ub, $UbL^{DSK}$, $UbL^{HRA}$ and $UbL^{HRB}$. Yeast strains expressing the GST linked proteins as well as Pre1-FLAG, FIG. 13B. The blot was developed with anti-FLAG antiserum (KODAK). The position of molecular weight markers are indicated.

In FIG. 14A GST-$UbL^{HRA}$ and GST-$UbL^{HRB}$ were purified and incubated with Hela cell S100 extract. Lane 1 contains a GST negative control, while lanes 2 and 3 contain GST-$UbL^{HRA}$ and GST-$UbL^{HRB}$. Lane 4 contains GST-$UbL^{R23}$ interacting proteins. Hela S100 extracts were incubated with GST, GST-$UbL^{HRA}$ and GST-$UbL^{HRB}$ and bound proteins were separated by SDS-PAGE and the western blot incubated with Cim5-specific antibodies, which cross-reacts with the human counterpart Mss1. In FIG. 13B, a similar set of GST linked proteins were incubated with purified 19S/PA700 and the bound proteins separated by SDS-PAGE and visualized by staining with silver nitrate. The profile of subunits that comprise the 19S/PA700 particle is shown in lane 1. Molecular weight standards are indicated in lane 5. (Lanes 1-5 were from the same gel).

FIGS. 19A and 19B show amino acid sequence alignments of UbL-domain containing sequences and common features amongst these proteins (SEQ ID NO:1 and SEQ ID NO:2). FIG. 19A shows an alignment of UbL domains from ubiquitin (Ub; SEQ ID NO:3); yeast Dsk2 (DSK; SEQ ID NO:4); yeast Rad23 (RAD; SEQ ID NO:5); Human Rad23-B (HHR23-B; SEQ ID NO:6); Human Rad23-A (HHR23-A; SEQ ID NO:7); yeast protein containing an internal UbL (212; SEQ ID NO:8); and yeast ubiquitin-like protein that is post-translationally conjugated to other proteins (RUB1; SEQ ID NO:9). FIG. 19B shows an alignment of SUMO1 (SEQ ID NO:10), which is a mammalian homolog of yeast SMT3; SMT3B (SEQ ID NO:11), SMT3A (SEQ ID NO:12), and SMT3 (SEQ ID NO:13) from yeast, which is a ubiquitin like protein that is post-translationally conjugated to other proteins like ubiquitin and RUB1.

DETAILED DESCRIPTION OF THE INVENTION

Figure 1A:
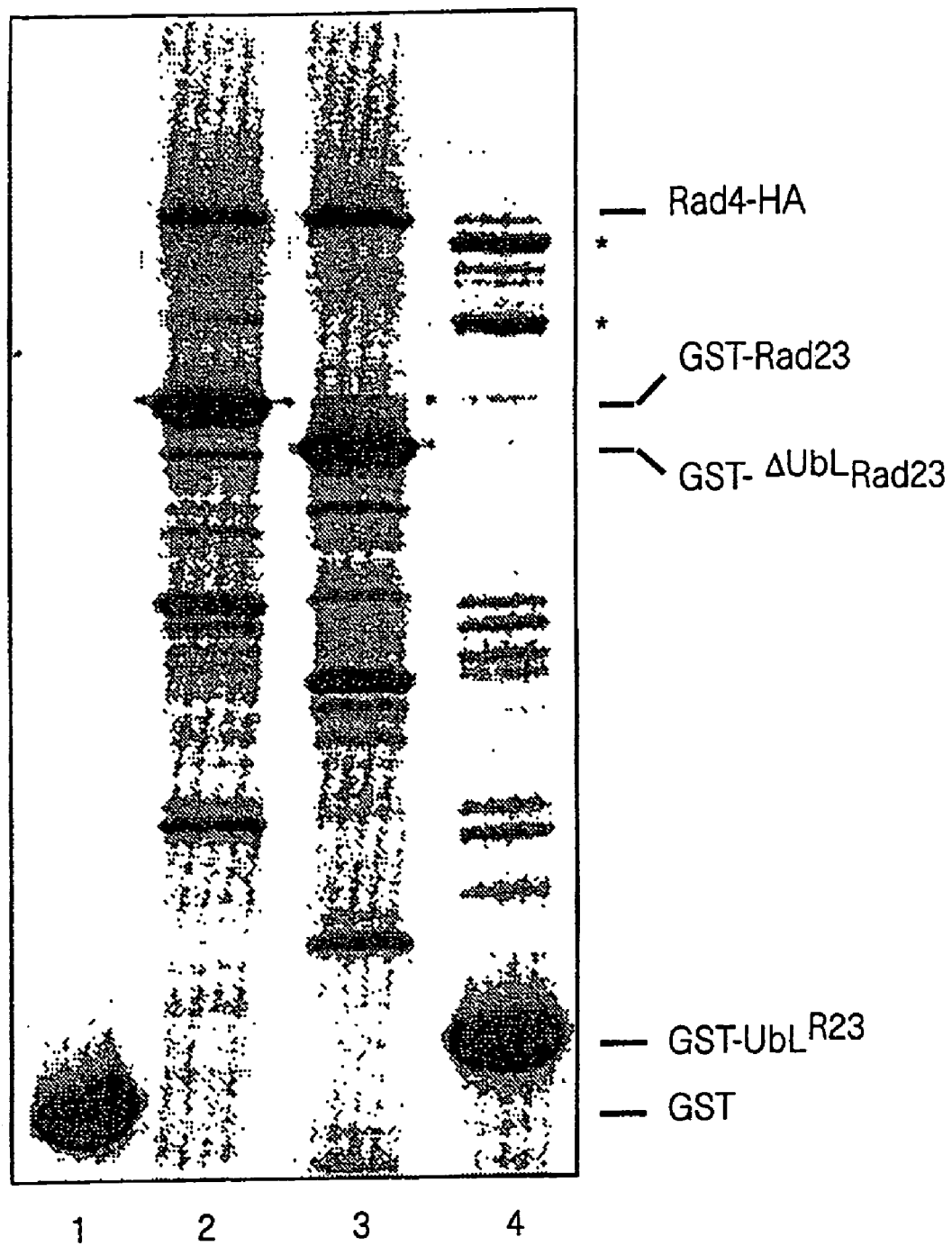
FIGS. 1A-1E show an autoradiograph and western blots of cell extracts showing that Rad4-HA interacts with Rad23 and that Rad23 interacts with the 26S proteasome. Rad4 plays a role in DNA repair and stably interacts with Rad23.

The proteasome is an essential component of the ATP-dependent proteolytic pathway in eukaryotic cells and is responsible for the degradation of most cellular proteins. The 20S (700 kDa) proteasome contains multiple peptidase activities that function through a new type of proteolytic mechanism involving a threonine active site. The 26S (2000 kDa) complex, which degrades ubiquitinated proteins, contains, in addition to the 20S proteasome, a 19S regulatory complex composed of multiple ATPases and components necessary for binding protein substrates. The proteasome has been highly conserved during eukaryotic evolution, and simpler forms are found in archaebacteria and eubacteria.

The post-translational attachment of ubiquitin (Ub) to cellular proteins is implicated in a broad range of biological activities primarily involving protein degradation (Hershko (1991) *Trends Biochem. Sci.* 16:265-268). Ubiquitin is mobilized through several trans-thiolation steps which precede its isopeptide linkage to cellular substrates. Ubiquitin is activated by adenylation of its C-terminal glycine residue by the ubiquitin activating enzyme, E1 (Hershko (1991) supra). Activated Ub is transferred from E1 to a family of ubiquitin-conjugating enzymes (E2's or Ubc's) which play significant roles in substrate selection. Emerging evidence suggests that the transfer of Ub to a cellular substrate may require an additional factor termed E3/Ub-protein ligase (Hershko (1991) supra; Scheffner, et al. (1995) *Nature* 373:81-83), or Ubr1/n-recognin (Varshavsky (1992) *Cell* 69:725-735). A well-studied substrate targeting mechanism of the ubiquitin system is the N-end rule pathway (Varshavsky (1992) supra), whose overexpression inhibits the growth of haploid yeast cells (Madura and Varshavsky (1994) *Science* 265:1454-1458). RAD23, a subunit of the nucleotide excision repair complex was isolated in a search for suppressors of this growth defect. The present invention describes the biochemical analysis of alleles of Rad23 (Rad23-HA and Rad23-FLAG). It appears from these studies that Rad23 is involved in both DNA repair and the ubiquitin protein degradation pathway.

Previous studies have demonstrated that mutations in RAD23 (rad23Δ) result in a defect in the repair of UV-irradiated DNA, which is manifested by an intermediate sensitivity to DNA damage (Friedberg, et al. (1995) DNA Repair and Mutagenesis. American Society for Microbiology, Washington, D.C.). The moderate sensitivity of rad23 to UV light is contrasted by the severe defects observed in other excision repair mutants such as rad1, rad2 and rad4 which are unable to incise damaged DNA (Wilcox and Prakash (1981) *J. Bacteriol.* 148:618-623). The removal of DNA lesions is markedly reduced in rad23Δ but not abolished, suggesting that Rad23 plays an accessory role in nucleotide excision repair. In vitro studies showed that Rad23 forms a stable interaction with the excision repair protein Rad4 (Guzder, et al. (1995) *J. Biol. Chem.* 270: 12973-12976), although the biological significance of this association is unclear. Rad23 also interacts with other effectors, including the DNA damage-recognition protein Rad14 and the RNA PolII-specific transcription factor TFIIH (Guzder, et al. (1995) *J. Biol. Chem.* 270:8385-8388). A previously unknown function for Rad23 in spindle-pole body (SPB) duplication has been described (Biggins, et al. (1996) *J. Cell Biol.* 133:1331-1346). These results indicate that Rad23 can participate in multiple regulatory pathways.

It has now been discovered that the Rad23 N-terminal domain (UbL$^{R23}$) has a strong affinity for the 26S-proteasome and can be used to purify this proteolytic complex in a single step. Immobilizing this domain to a solid support, followed by exposure to cellular lysates results in the retention of the proteasome on the support. The proteasome can then be released from the support following the prior elution of all other non-specifically adsorbed proteins. A family of proteins having Ub-like domains have been observed in a variety of other species from yeast to humans (Toniolo, et al. (1988) *Proc. Natl. Acad. Sci. USA* 85:851-855; Wiborg, et al. (1985) *EMBO J.* 4:755-759). Ubiquitin-like domains in yeast Rad23 and Dsk2, as well as human HHR23A and HHR23B, are proteasome-interacting sequences. The attachment of UbL$^{R23}$ to a reporter protein also targeted it to the proteasome, demonstrating that this is an autonomous function of an UbL. The ubiquitin-like domain of Rad23 (UbL$^{R23}$) interacts with a complex that contains subunits of the 26S proteasome and displays ATPase and protease activities expected for this proteolytic system. In agreement with this finding, proteasome-specific inhibitors caused marked reduction in the proteolytic activity associated with UbL$^{R23}$. The ubiquitin-like domain of Dsk2 (UbL$^{DSK}$) binds the proteasome preferentially in actively growing cells. Overexpression of UbL$^{R23}$ inhibits the degradation of specific substrates of the ubiquitin pathway perhaps by saturating the proteasome targeting pathway. These results indicate that the physiological roles mediated by proteins containing ubiquitin-like motifs converge at the level of the proteasome. The use of these ubiquitin-like homolog sequences for the purification of proteasomes from corresponding cell types (e.g., human UbL-domains to purify human proteasomes or yeast UbL-domains to purify yeast proteasomes) is contemplated to be within the scope of the invention.

Kits are provided for purifying proteasomes from a variety of cell types. Such kits would include predetermined UbL domains fused to a solid support. The kit of the invention can also conveniently include a device for purifying biological samples, together with various solutions which may be used in performing the purification procedure, such as buffer(s), saline, diluent, controls and the like.

In accordance with another aspect of the present invention, it has been discovered that the stability, as determined by protein half-life, of Rad23-HA is tightly regulated, ranging from approximately 1 minute in proliferative (i.e., actively growing) cells to greater than 1 hour in stationary-phase or quiescent cells. In contrast to the instability of the epitope-tagged Rad23-HA allele, it was previously reported that native Rad23 is stable (Watkins, et al. (1993) *Mol. Cell. Biol.* 13:7757-7765). Data presented herein reveal that Rad23 is degraded during the G1/S phase of the cell cycle. Specifically, data are described which indicate that the ubiquitin-like domain of Rad23 (UbL$^{R23}$) is an autonomous and regulated degradation signal. Two additional lines of evidence indicate a direct interaction with the proteolytic apparatus: 1) Rad23 interacts with Irt1, a protein that has strong similarity to ATPase subunits of the 26S proteasome, and 2) immunopurified 26S proteasome contains native Rad23. Thus, the findings presented herein indicate a proteolytic function for Rad23.

Malignant cells display aberrant growth properties and do not respond to normal regulatory signals. Malignancy therefore arises because aberrant cells continue to grow in conditions when normal cells remain quiescent. Detection and treatment of proliferative disorders must begin with the clear identification of proliferative cells that manifest aberrant growth rates. Although malignant cells are often morphologically distinguishable from their wild-type counterparts, a quantitative method for detecting proliferative cells is lacking.

Thus, one embodiment of the present invention embraces methods employing UbL domain-reporter fusion protein(s) to detecting proliferative cells of evolutionarily divergent organisms from yeast to humans. UbL-reporter fusion proteins in rapidly dividing or proliferative cells are degraded rapidly (i.e., the fusion proteins are unstable) whereas those in quiescent cells (i.e., control cells) remain stable. Thus, fusion protein stability, based upon the half-life of the fusion protein within the cell, is indicative the growth rate of the cell. As used in the context of the present invention, a reporter protein can include a selectable marker, as well as a protein that confers drug resistance. In these types of assays, cells that stabilize a UbL domain fusion protein produced from a DNA construct composed of a UbL domain coding sequence linked to a drug resistance gene would survive in the presence of the drug. In contrast, proliferating cells would actively degrade the fusion protein and succumb to the presence of the drug. In a quantitative assay such as this, dose titrations are employed to define the conditions that promote the killing of malignant cells without harming normal cells.

By way of illustration, the ubiquitin-like domain $UbL^{R23}$ was operably linked to the reporter protein β-galactosidase ($UbL^{R23}$-LacZ) to assess whether a cell with a catalytically active 26S proteasome is quiescent or proliferative. Growth-dependent degradation of native Rad23 was observed. These data indicated that $UbL^{R23}$ was an important component of the degradation signal. As proposed, $UbL^{R23}$-LacZ fusion proteins proved to be exceedingly unstable in proliferative cells but entirely stable in quiescent cells, mimicking the degradation profile of Rad23 protein.

To further assess the suitability of using $UbL^{R23}$-LacZ fusion proteins to detect proliferative cells, this fusion protein was produced in cells expressing various Ras mutants. Ras proteins are highly conserved small GTP-binding regulators that control growth, differentiation and a variety of other cellular functions. Oncogenic alleles of Ras are hyperactive and do not arrest growth properly, while null mutants of Ras arrest growth prematurely. The data revealed that the level of $UbL^{R23}$-LacZ was almost undetectable in a strain expressing the oncogenic Ras mutant, while elevated levels of $UbL^{R23}$-LacZ were detected in cells lacking Ras. These findings confirm that $UbL^{R23}$-LacZ is a suitable reporter protein to detect proliferative cells.

The strategy described above enables the identification of genetic mutants that promote or attenuate the degradation of the UbL-linked chimeras. Such mutants would either promote or inhibit proliferation. This method also provides a way to screen for compounds that promote quiescence. For instance, if an UbL is linked to a gene that confers drug resistance, the expression of drug resistance should be confined to quiescent cells, or cells whose growth has been artificially arrested.

In yet another aspect of the present invention, it has been discovered that the $UbL^{R23}$ domain confers thermostability on Rad23 and on fusion proteins to which this domain has been operably-linked. Thus the UbL domain is a cis-acting temperature stabilizer. This domain can be used to advantage to create fusion proteins with enhanced thermostability.

PCR assays utilize the Taq polymerase enzyme which functions at the higher temperatures required for PCR yet also generates errors in the amplified sequences as the enzyme exhibits reduced fidelity in DNA copying. In one embodiment of the invention, the UbL domain is fused to a polymerase enzyme which has a reduced error rate. Such fusion proteins can be used in PCR assays to increase the fidelity of DNA amplification.

As used in the context of the present invention, the term proteasome refers to a 26S multicatalytic protease. As is well-known in the art, a defect (e.g., loss of function mutation) in any one of the subunits (e.g., ATPase subunits) of the 26S proteasome generally results in lethality, including conditional and synthetic lethality (see, e.g., Seeger, et al. (1996) *J. Mol. Biol.* 263(3):423-31; Saito, et al. (1997) *Gene* 203(2): 241-50; Fujimuro, et al. (1998) *FEBS Lett.* 423(2):149-54; Takeuchi and Toh-e (1999) *Mol. Gen. Genet.* 262(1):145-53; Hilt, et al. (1993) *J. Biol. Chem.* 268(5):3479-86). In contrast, a gain-of-function in this pathway is associated with a proliferative growth phenotype, e.g., as found in tumor cells (Okamoto, et al. (2003) *Cancer Res.* 63(14):4167-73; Almond and Cohen (2002) *Leukemia* 16(4):433-4; Ichihara, et al. (1993) *Adv. Enzyme Regul.* 33:173-80). Thus, particular embodiments embrace that cells assayed in accordance with the present invention have a catalytically active 26S proteasome. A catalytically active 26S proteasome is used herein to refer to a proteasome exhibiting measurable activity, e.g., to degrade UbL containing proteins. As such, a cell with a catalytically active 26S proteasome would exclude cells having proteasome mutations which are apparent only as conditional or synthetic lethal mutations.

The phrase "N-end rule pathway" relates the in vivo half-life of a protein to the identity of its amino-terminal residue. Overexpression of targeting components of the N-end rule pathway in *S. cerevisiae* inhibits the growth of yeast cells.

The term "promoter region" refers to the 5' regulatory regions of a gene. In the present invention, the use of both strong constitutive gene promoters and inducible gene promoters is contemplated.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector. The term may also be used to describe the fusion of a nucleic acid sequence encoding an UbL domain of the invention to a second nucleic acid sequence encoding a protein of interest (e.g., a reporter protein). Expression of the fused nucleic acid sequences results in the production of a fusion protein.

The term "fusion protein" refers to a chimeric protein molecule comprising two or more domains from different sources.

The term "DNA construct" refers to genetic sequence used to transform cells. These constructs may be administered to cells in a viral or plasmid vector.

The term "reporter" or "reporter gene" refers to a protein or gene, respectively, whose expression can be assayed for; such reporters include, without limitation, lacZ, amino acid biosynthetic genes, e.g., the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available.

The term "selectable marker" refers to a gene product that when expressed confers a selectable phenotype such as antibiotic resistance on a transformed cell.

Methods of delivery of the DNA constructs of the invention to target cells include electroporation, $CaPO_4$ precipitation, lipid-based systems and microinjection. Standard methods for delivery of DNA and protocols for preparing the transforming DNA may be found in Current Protocols in Molecular Biology, eds. Frederick M. Ausubel et al., John Wiley & Sons, 1995.

The following specific examples are provided to illustrate various embodiments of the invention. They are not intended to limit the scope of the invention in any way.

Example 1

Rapid and Efficient Purification of Proteasomes Using Rad23 and Components thereof Rad23 has an unusual N-terminal domain that bears a striking resemblance to ubiquitin (Watkins, et al. (1993) supra). This domain, which has been designated UbL$^{R23}$, is important for DNA repair because its elimination causes sensitivity to UV light (Watkins, et al. (1993) supra). A role for Rad23 in the ubiquitin system has been suggested by its suppression of N-end rule induced toxicity, which raised the possibility of a proteolytic function in DNA repair.

Rad23 and Rad4, as well as the human counterparts HHR23-B and XPC, form stable interactions. It was therefore tested whether GST-Rad23 interacts with components of the DNA repair and proteolytic pathways. Rad4 was linked to the HA epitope (Tyr-Pro-Tyr-Asp-Val-Pro-Asp-Tyr-Ala; SEQ ID NO:14 (Rad4-HA)) and was found to complement rad4Δ. GST-Rad23 and Rad4-HA were expressed simultaneously in yeast cells and metabolically labeled with [$^{35}$S]-methionine. Radiolabeled extracts were applied to glutathione-SEPHAROSE and bound proteins analyzed by SDS-PAGE and fluorography. Rad4-HA interacts with GST-R23. See FIG. 1A, lane 2. The interaction of Rad4-HA with GST-Rad23 did not require UbL$^{R23}$, (FIG. 1A, lane 3) demonstrating that distinct regions of Rad23 interact with the proteolytic and DNA repair pathways. Identical samples were transferred to nitrocellulose and analyzed by incubation with anti-HA antibodies and, consistent with these findings, RAd4-HA was detected only in lanes 2 and 3.

Figure 1B:
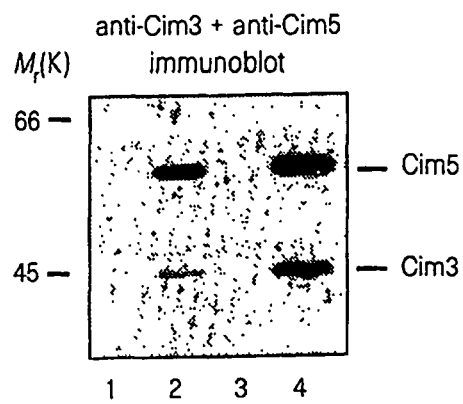
Figure 1C:
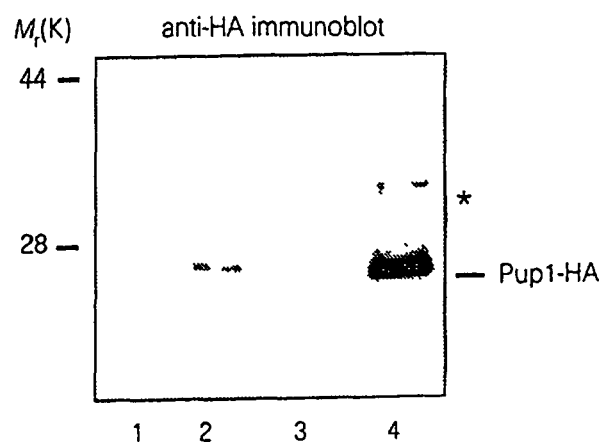
Figure 1D:
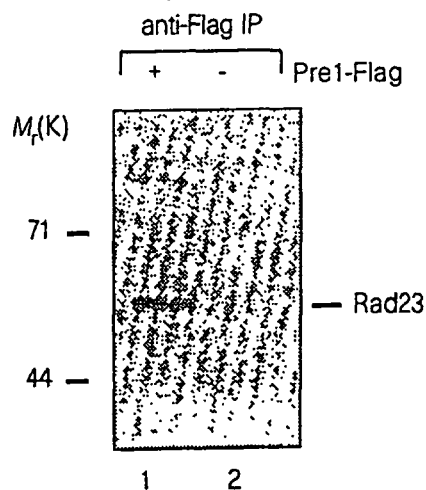
Figure 1E:
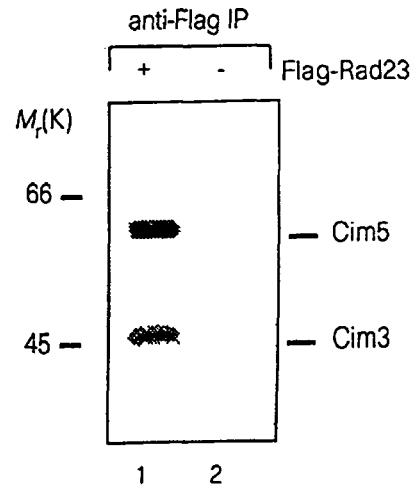

To further explore the proteolytic function of Rad23 in DNA repair, Rad23 and two truncated mutants were operably linked to glutathione-S-transferase (GST-Rad23, GST-$^{ΔUbL}$Rad23, and GST-UbL$^{R23}$), and immobilized on glutathione-SEPHAROSE. Western blots containing the proteins released from GST and GST-Rad23 beads were incubated with antibodies against Cim3 (Sug1) and Cim5. Cim3 and Cim5 are ATPases of the regulatory (19S) subunit of the 26S proteasome. Both Cim3 ($M_r$ 43K) and Cim5 ($M_r$ 54K) were detected in the GST-Rad23 beads (FIG. 1B, lane 2) but not in the control GST beads (FIG. 1B, lane 1). GST-UbL$^{R23}$ alone could efficiently bind a complex containing Cim3 and Cim5 (FIG. 1B, lane 4) but, a mutant lacking UbL$^{R23}$ (GST-$^{ΔUbL}$Rad23) could not (FIG. 1B, lane 3). Two variants of Rad23, bearing small epitopes on either the N-terminus (FLAG-Rad23, FIG. 1E) or the C-terminus (Rad23-HA) also interacted with the proteasome. Both Cim3 and Cim5 were detected in anti-FLAG immunoprecipitates prepared from yeast cells expressing FLAG-Rad23 (FIG. 1E). Because yeast cells expressing $^{ΔUbL}$Rad23 fail to complement rad23Δ, these findings indicate that Rad23-proteasome interaction is important for DNA repair. These data also show that UbL$^{R23}$ represents a new proteasome interaction signal. A large family of proteins bearing ubiquitin-like extensions have been identified (see FIG. 19), and these results indicate that these protein have proteolytic functions.

To determine whether the GST-Rad23 interacting complex included 20S catalytic subunits, extracts from cells expressing Pre1-FLAG (28K) or Pup1-HA (33K), both of which are epitope-tagged derivatives of 20S β-subunits were analyzed. Both Pup1-HA (FIG. 1C, lane 2) and Pre1-FLAG were detected in GST-Rad23 beads after incubation with FLAG or HA antibodies, confirming the presence of 20S catalytic subunits. GST-UbL$^{R23}$ accumulated to higher levels than GST-Rad23, and the recovery of Pup1-HA was proportionately higher (FIG. 1C, compare lanes 2 and 4). To confirm that the findings applied to native Rad23, Pre1-FLAG was immunoprecipitated on FLAG-agarose beads and interacting proteins were resolved on SDS-PAGE. Proteins were transferred to nitrocellulose and the blots were incubated with Rad23-specific antibodies. Native Rad23 was readily detectable in immunoprecipitates containing Pre1-FLAG but not from a control extract lacking this epitope-tagged proteasome subunit (FIG. 1D). Approximately 5% of cellular Rad23 precipitated with Pre1-FLAG. This estimate is based on the amount of Rad23 that remained on the FLAG-agarose beads after 18 hours at 4° C. The in vivo interaction could be higher if the interaction with the proteasome is transient or regulated.

To examine if the Rad23 interacting complex had proteasome-specific activities, ATPase (Merrick (1979) Meth. Enzymol. 60:108-123), and protease activities (Heinemeyer, et al. (1991) EMBO J. 10:555-562) were measured. It was found that high levels of ATPase activity were associated with FLAG-Rad23 (Kibel, et al. (1995) Science 269:1444-1446). Consistent with this finding, high proteolytic activity was detected against three different peptide substrates in FLAG-Rad23 immunoprecipitates. This activity was significantly reduced by the proteasome inhibitors MG132 and lactacystin (Coux, et al. (1996) Annu. Rev. Biochem. 65:801-847). See FIG. 2.

Figure 3A:
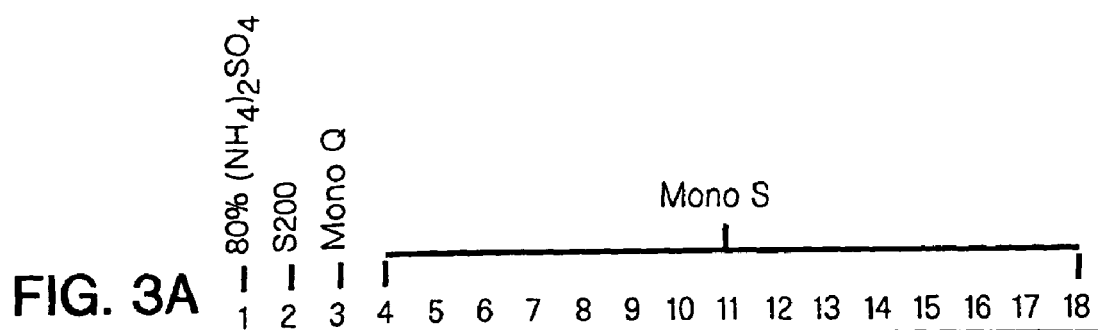
FIG. 3A is a COOMASSIE stained gel showing MONO-S fractions isolated following incubation with glutathione-SEPHAROSE. Bound proteins were separated by SDS-PAGE.
Figure 3B:
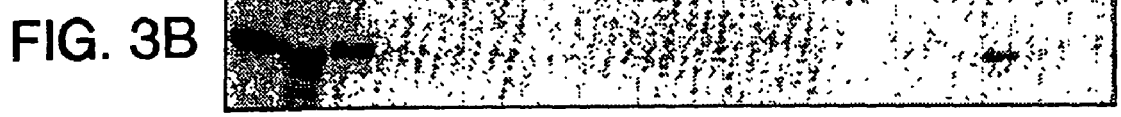
Figure 3C:
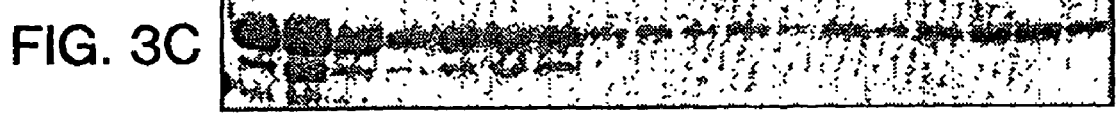

To characterize the interaction of Rad4 with Rad23, extracts were prepared from cells expressing both GST-Rad23 and Rad4-HA and proteins separated on SEPHACRYL S-200. GST-Rad23 was detected in the void volume coincident with dextran blue, and also in fractions corresponding to its predicted monomeric size (approximately 80 K). GST-Rad23, Cim5 and Rad4-HA could each be detected in the high molecular weight fraction, indicating that they are components of a single complex. See FIGS. 3A-C, lane 2.

Figure 3D:
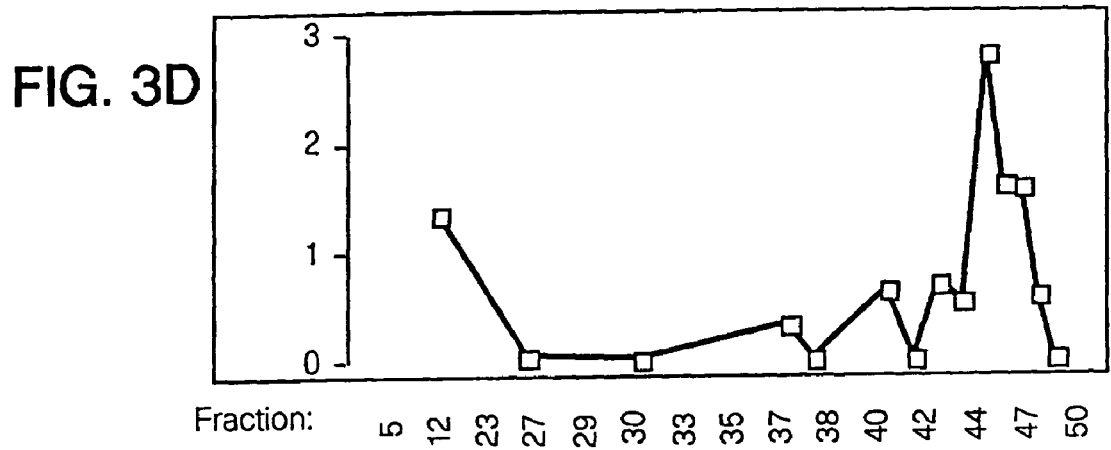
FIG. 3D is a graph showing the ATPase activity corresponding to the MONO-S fractions isolated.

To investigate this further, proteins in the SEPHACRYL S-200 void volume were chromatographed on MONO-Q. GST-Rad23, Rad4-HA, and Cim5 were detected in samples eluting at approximately 0.35M KCl. Significantly, these fractions were previously shown to contain catalytically active proteasome (Rubin, et al. (1996) Nature. 370:655-657). Fractions that eluted between 325 and 375 mM KCl from the MONO-Q column were pooled and chromatographed on MONO-S. Cim5 and Rad4-HA again co-fractionated with GST-Rad23 (FIGS. 3A-3C, lanes 15-18) and a peak of ATPase activity co-purified with the GST-Rad23 interacting complex. See FIGS. 3D.

Figure 4:
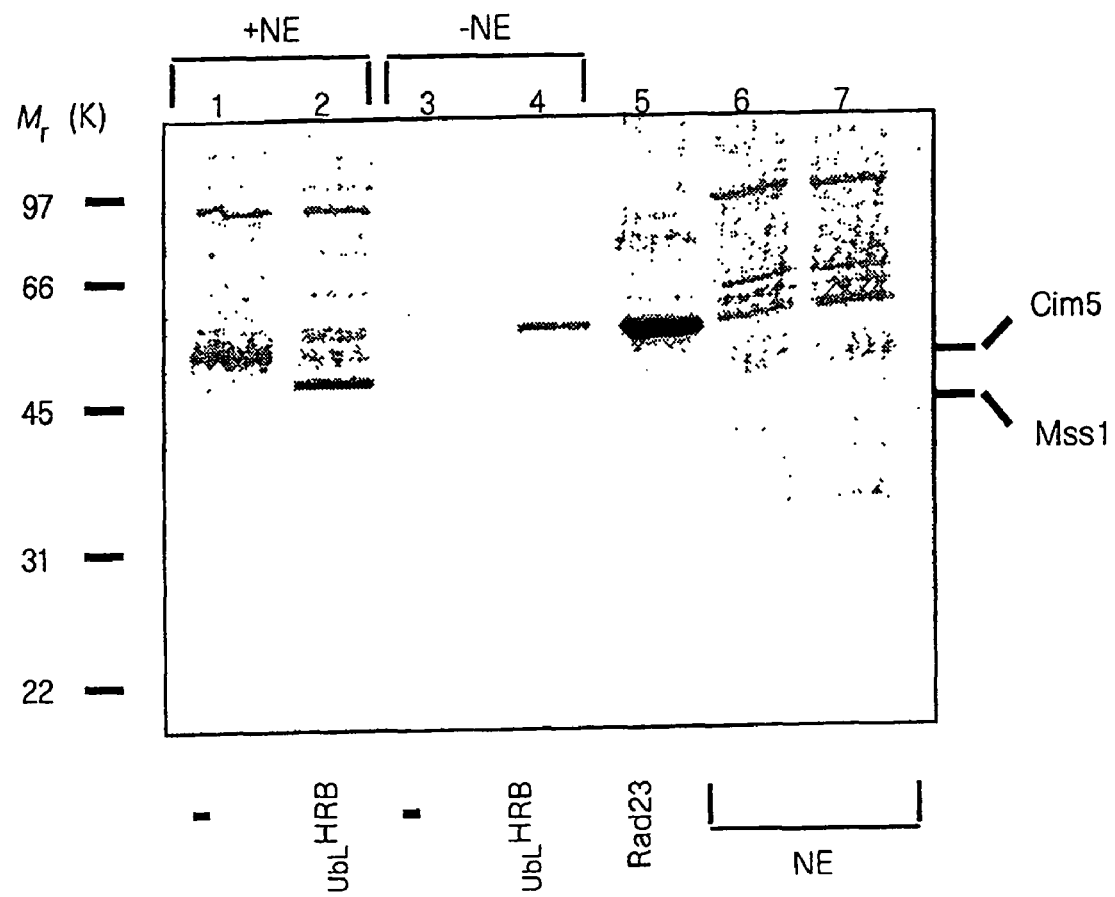
FIG. 4 is a blot showing that human HHR23-B interacts with Mss1. The ubiquitin-like domain of HHR23-B was linked to GST (GST-Ub$^{HRB}$) and incubated with Hela cell nuclear extracts. Mss1 was detected with Cim5 antibodies (lane 2), Cim5 interaction with GST-R23 is also shown (lane 3).

As mentioned previously, two human homologues of Rad23, HHR23-A and HHR23-B contain N-terminal ubiquitin-like domains, indicating that they act in a similar way to the yeast protein, Rad23. Significantly, HHR23-B forms a stable interaction with XPC, the human counterpart of Rad4. To explore the functional relatedness of HHR23-A and HHR23-B proteins with Rad23, the ubiquitin-like domain of HHR23-B (UbL$^{HRB}$) was linked to GST. GST-UbL$^{HRB}$ was immobilized on glutathione-SEPHAROSE and reacted with nuclear extracts prepared from Hela cells. Cim5 antibodies revealed an interaction between GST-UbL$^{HRB}$ and Mss1, the human equivalent of Cim5. See FIG. 4, lane 2. GST-Rad23 interaction with Cim5 (lane 4) confirmed the specificity of the antibody reaction. The evolutionary conservation of yeast and human DNA repair and ubiquitin pathways indicates that the molecular interactions reported here are evidence of a novel mechanism for regulating DNA repair common in both yeast and humans. These findings also indicate that ubiquitin-like sequences represent a novel class of proteasome-interacting domains.

As exemplified herein, UbL-like domains can be used to efficiently purify the proteasome. This rapid purification method enables purification from a variety of cell types. The UbL-domains can be immobilized to a solid support such as an immunoaffinity column. Following immobilization, the column is exposed to cell lysates, non-specific proteins are eluted and the immobilized proteasome subsequently purified.

Exemplary UbL-domain containing sequences for use in the methods of the present invention are depicted in FIG. 19. As is evident from the alignment of these UbL-domains, UbL domains share the common structural motifs of (Lys/Arg)-Leu-(Leu/Ile)-Xaa$_1$-Xaa$_2$-Gly-Lys-Xaa$_3$-(Leu/Ser)-Xaa$_4$-Asp (SEQ ID NO:1), wherein Xaa$_1$ is a hydrophobic amino acid (e.g., Phe, Tyr, Leu), Xaa$_2$ and Xaa$_3$ are any amino acid residue, and Xaa$_4$ is a polar amino acid residue; and (Lys/Gln)-(Ala/Ser)-(Phe/Tyr)-(Cys/Ala)-Xaa$_1$-Arg-Gln-Gly (SEQ ID NO:2), wherein Xaa$_1$ is a polar amino acid residue (e.g., Glu, Gln, or Lys). Accordingly, particular embodiments embrace the use of a UbL domain containing the amino acid sequence set forth in SEQ ID NO:1 or SEQ ID NO:2.

Example 2

Rad23 and its Role in Protein Degradation

Nucleotide excision repair is enhanced by Rad23, a member of a class of proteins that bear unusual ubiquitin-like domains at their N-termini. Specific modifications of Rad23 cause rapid degradation via the ubiquitin/proteasome system. Unexpectedly, the short in vivo half-life of these variants does not affect the DNA damage response and can be reconciled with a growth-stage-specific function for Rad23. The degradation signal in Rad23 resides in its N-terminal ubiquitin-like domain (UbL$^{R23}$), which confers instability when placed on a heterologous protein. Evidence for a proteolytic function for Rad23 is indicated by its interaction with Irt1p, a protein that bears a striking resemblance to members of the ATPase subunits of the 26S proteasome. Rad23 can be co-precipitated with immunopurified 26S proteasome, implicating a proteolytic function during DNA repair.

Isolation of High-copy Suppressors of N-end Rule Overexpression. Yeast strain KMY950 was generated by transforming JD47-13C with a 2 μm-based plasmid expressing UBR1 and UBC2 from the galactose-inducible GAL1/10 promoter. The growth of KMY950 is severely impaired on galactose-containing medium due to overexpression of the N-end rule pathway (Madura and Varshavsky (1994) Science 265:1454-1458). KMY950 was transformed (Gietz, et al. (1992) Nuc. Acids Res. 20:1425-1434) with a plasmid library expressing yeast cDNAs from the GAL1 promoter (Liu, et al. (1992) Genetics 132:665-67). Based on control plating experiments, it was estimated that a total of approximately 10$^5$ transformants were analyzed. Plasmid DNAs that enabled KMY950 to grow on galactose-containing medium were identified and subjected to sequence analysis by the dideoxy chain-terminating method. One strong suppressor (plasmid pCEP10) encoded the complete open reading frame of the yeast RAD23 gene.

Strains, Media, Growth Conditions and Genetic Techniques. S. cerevisiae strains include JD47-13C (MATa his3-Δ200 leu2-2, 112 ura3-52 trp1-Δ63 lys2-801); CSY85 (rad23Δ::URA3 in JD47-13C); CSY228 (5-FOA cured ura$^-$ derivative of CSY85); BR4 (MATα pre1-1 pre2-2 ura3-Δ5 leu2-2, 112 his3-11, 15); RY262 (MATα his4-518 ura3-52 rpb1-1); BJ5457 (MATα ura3-52 trp1 lys2-801 leu2-Δ1 his3-Δ200 pep4::HIS3 prb1Δ1.6R can1); Y791 (MATa his3-Δ200 leu2Δ1 ura3-2 cim5-1); KMY334 (MATa his7 cdc7-4 ura3 bar1-1); CTY10-5d (MATa ade2 gal4 gal80 his3-Δ200 leu2-3, 112 trp1-Δ901 URA3-lexop GAL1-LacZ). The ubc4Δ, ubc5Δ, ubc4Δ ubc5Δ and the congenic wild-type strains are known in the art. A rad4Δ::URA3 deletion was made in MKP°; (MATα ade2 lys2 can1-100 his3-Δ200 ura3-52 trp1-Δ901 leu2-2, 112). E. coli strain MC1066, bearing the pyrF74:pn5 mutation was used to select plasmids expressing yeast URA3. Yeast growth media were prepared as described previously (Guthrie and Fink (1991) Guide to Yeast Genetics and Molecular Biology. Academy Press, New York). The expression of genes linked to the CUP1 promoter was induced by the addition of 0.1 mM CuSO$_4$. For pulse-chase analysis exponential-phase cells were grown to a density at A$_{600}$ of approximately 0.5 and stationary phase cultures were grown to A$_{600}$>2.5. In experiments where the stability of Rad23-HA was measured in both conditions, stationary-phase cultures were collected (25 ml) by centrifugation, washed and resuspended in a small volume of sterile dH$_2$O. The cell suspension was inoculated into the used stationary-phase medium and fresh YPD medium, and incubated with vigorous aeration at 30° C. for 4-5 hours to enable the YPD cultures to resume exponential growth. After 4 hours at 30° C., the density of the YPD culture increased by approximately 2-fold, indicating recovery from stationary phase.

Plasmids, DNA Manipulations and DNA sequencing. Recombinant methods were performed by standard procedures (Ausubel (1992) supra). RAD23 was amplified by polymerase chain reaction (PCR) using oligonucleotide primers (#42: 5'-GCG AAT TCA TGG TTA GCT TAA CC-3'; SEQ ID NO: 15) and #41: 5'-GCG GTA CCC GTC GGC ATG ATC GCT G-3'; SEQ ID NO:16). The primers introduced an EcoRI site on the 5' end and a KpnI site on the 3' end of the DNA fragment. A 1.2 kb EcoRI-KpnI PCR DNA fragment was ligated to EcoRI/KpnI-digested pKM1362-2 (Madura and Varshavsky (1994) supra), yielding plasmid pCS8. In pCS8, Rad23p is linked to a C-terminal HA-epitope (Rad23-HA) and is expressed from the CUP1 promoter. To construct rad23Δ, a 4.8-kb EcoRI fragment containing a disrupted allele of RAD23 was excised from pDG28 (Madura and Prakash (1990) Nuc. Acids Res. 18:4737-4742) and used to replace the wild-type gene in JD47-13C by homologous recombination (Rothstein (1991) Methods Enzymol. 194:281-301). The resulting rad23Δ::URA3 strain (CSY85) was plated on 5-FOA containing medium to isolate CSY228, a ura-derivative (Boeke, et al. (1984) Mol. Gen. Genet. 197: 345-346). To make Rad23-HA lacking its N-terminal ubiquitin-like domain (pWP1), DNA sequence encoding codons 78 to 398 were amplified using oligonucleotide primers (#88: 5' GCG AAT TCA TGA CGA AGA CCA AAC TAA CAG AA-3'; SEQ ID NO:17, and #41: SEQ ID NO:16) and ligated to pKM1362-2, as described above. Similarly, DNA sequence corresponding to codons 1-77 (UbL$^{R23}$) were amplified and ligated to LacZ in pKM1362-2 to yield UbL$^{R23}$-LacZ. Oligonucleotide primers, specific to the coding sequence of β-galactosidase gene (beginning at codon #8), were used to amplify LacZ.

Two-hybrid System Screen and Cloning of IRT1. RAD23 was isolated on a DraI-EcoRI DNA fragment, treated with DNA PolI-Klenow, and ligated to similarly treated BamHI digested pBTM116 (Paetkau, et al. (1994) *Genes & Dev.* 8:2035-2045). The resulting plasmid DNA, encoding lex-Rad23, was transformed into CTY10-5d. Yeast genomic DNA libraries were transformed into CTY10-5d expressing lexA-Rad23p and approximately $2.4 \times 10^5$ transformants were screened to identify blue colonies on indicator plates. Plasmid DNAs were purified from colonies that displayed an interaction (based on the color assay), and were subject to DNA sequence analysis using the primer 5'-GAA GAT ACC CCA CCA AAC-3' (SEQ ID NO:18), and then compared to sequences in GENBANK using the BLAST algorithm. The DNA sequence in plasmid pDG869 corresponded to an open-reading-frame designated YER047C on Chromosome V. A Lambda clone encompassing this region (#6379) was obtained from the American Type Culture Collection, and a 3.2 kb PstI DNA fragment was isolated and ligated to PstI digested pUC19 (pRK1). A 3.5 kb BssSI DNA fragment was purified from pRK1, treated with DNA PolI-Klenow, and ligated to the SmaI site in pUC8 (pRK16). A 3.2 kb EcoRI DNA fragment was isolated from pRK16 and ligated to EcoRI-treated pGAD424, to generate an in-frame fusion of Irt1p to the activation domain of Gal4 (pRK26). To generate C-terminal truncations of Irt1p, plasmid pRK26 was treated with Bsu361, BclI and NdeI and relegated to yield alleles encoding residues 1-567, 1-243 and 1-1.72, respectively. Measurement of β-galactosidase activity were as described in Paetkau et al. (1994) supra.

Pulse-chase and Immunoprecipitation. Pulse-chase analysis, protein extraction, quantitation and immunoprecipitation of HA-tagged and β-gal fusion proteins were carried out as described previously (Madura and Varshavsky (1994) supra). Yeast cells were labeled for 5 minutes with $^{35}$S-TRANSLA-BEL (ICN Pharmaceuticals), and the reaction was terminated by the addition of buffer containing cycloheximide and excess cold methionine and cysteine. Immunoprecipitations were carried out using equal cpm of lysate (that were adjusted to equal volume). Immune complexes were captured on Protein-A SEPHAROSE and resolved on SDS-polyacrylamide gels. Autoradiographic images were quantitated by PHOSPHORIMAGER analysis or densitometry. Rad23-HA was detected with HA-specific antibodies (Boehringer Manneheim, Inc.).

UV Irradiation and Survival Measurement. UV irradiation (at 254 nm) and estimation of survival were performed as described previously (Wilcox and Prakash (1981) *J. Bacteriol.* 148:618-623). Irradiated cells were allowed to recover in the dark for 3 days at 30° C.

Cell Cycle Arrest. Rad23-HA was expressed in a strain containing a temperature-sensitive allele of RNA polymerase II (RY262: rpb1-1). RY262 expressing Rad23-HA was grown at 23° C. in the presence of 0.1 mM $CUSO_4$ and then diluted 4-fold into YPD (+0.1 mM $CUSO_4$) that was equilibrated at 37° C., and incubated with vigorous aeration for 2 hours. Cells were collected by centrifugation and pulse-chase measurements were performed at 37°.

To measure the stability of Rad23-HA in $G_1$-arrested cells, Rad23-HA was expressed in KMY1012, a ura3 derivative of 4910-3-3A (Madura, et al. (1990) *Nuc. Acids Res.* 18:771-778). KMY1012 was grown at 23° C. to $A_{600}$ of approximately 0.3 and then suspended in YPD medium containing 10 ng/ml α-factor (Peninsula Labs). The culture was maintained at 23° C. for 3 hours until greater than 95% of α-factor treated cells were unbudded and arrested in $G_1$. Actively growing JD47-13C cells were treated with 100 μg/ml hydroxyurea (Sigma Chemical Co.) until greater than 75% of the culture displayed large dumbbell shaped cells. The arrested cells were subject to pulse-chase analysis as described earlier.

Rad23 Suppresses N-end Rule Toxicity. Overexpression of the N-end rule pathway causes growth inhibition which stems, at least in part, from the constitutive degradation of the essential Gα protein (Madura and Varshavsky (1994) supra). The degradation of Gα is believed to activate the mating-response pathway which causes growth arrest in $G_1$. In a screen to identify high-copy suppressors of N-end rule dependent toxicity, RAD23 was isolated. See FIG. 5A. It was expected that Rad23 might interact with the targeting components of the N-end rule pathway and thereby prevent Gα degradation. Such an interaction would indicate that Rad23 is a substrate of the N-end rule pathway, or a regulatory component of this proteolytic system. Two copies of the nine-residue HA epitope were linked to the C-terminus of Rad23. Rad23-HA conferred wild-type levels of UV resistance in rad23Δ, indicating that it is functionally competent. See FIG. 5B.

Figure 5A:
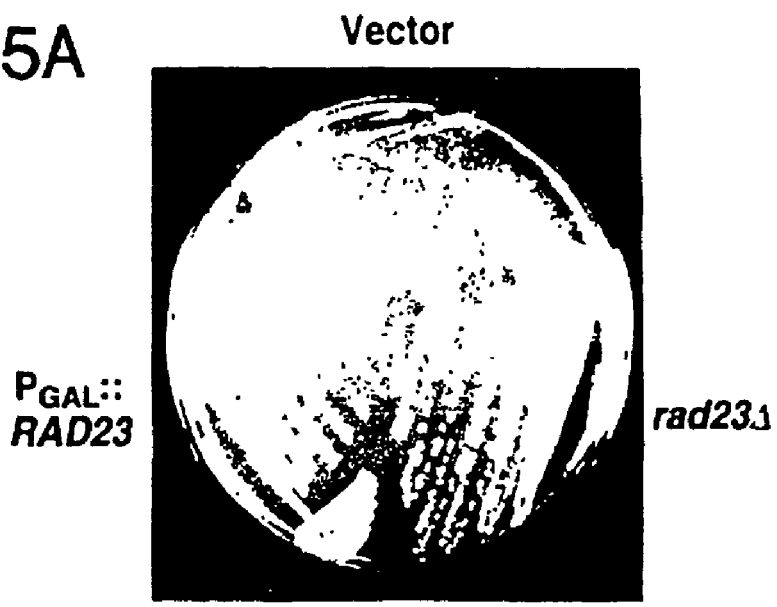
FIGS. 5A and 5B are data showing the genetic interaction between RAD23 and the N-end rule pathway.
Figure 5B:
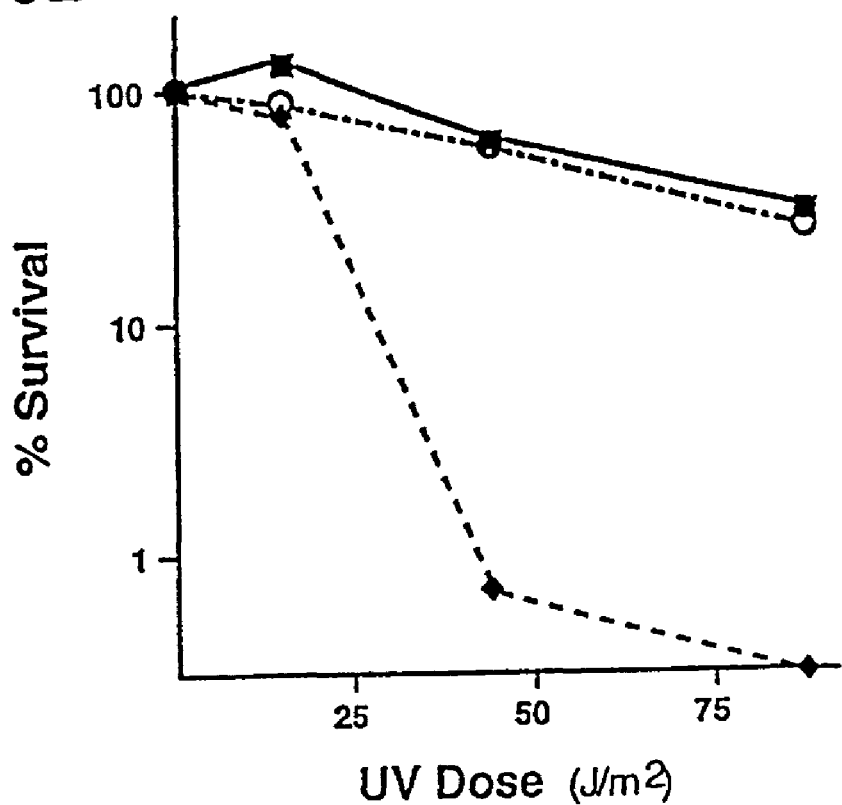
Figure 6A:
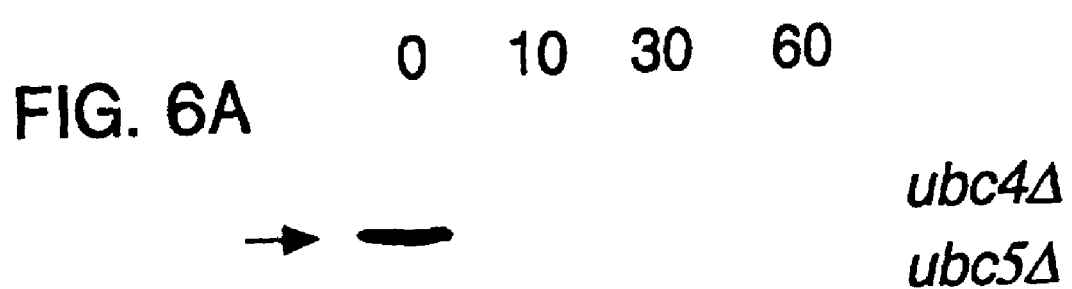
FIG. 6A hys-hows that Rad23-HA is unstable in ubc4Δ ubc5Δ suggesting that these E2 proteins do not affect its stability. Rad23-HA is also unstable in N-end rule pathway mutants, ubc2Δ (FIG. 6B) and ubr1Δ (FIG. 6C). The stability of Rad23-HA was comparable to that observed in the parental strain (FIG. 7A).
Figure 6B:
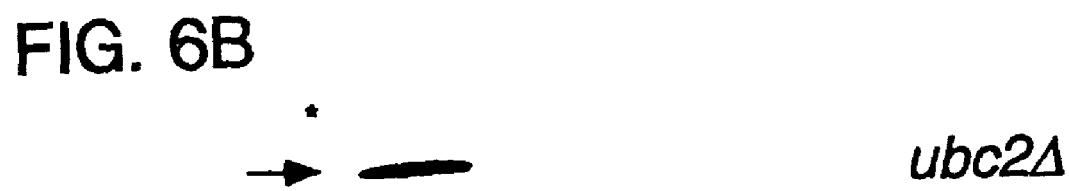
FIG. 6 is an autoradiograph showing the results of pulse-labeling experiments which indicate that Rad23-HA is not degraded by Ubc4 or the N-end rule system.
Figure 6C:

The stability of Rad23-HA was measured by pulse-chase analysis and found to be extremely short-lived in wild-type and ubr1Δ cells indicating that it is not a substrate of the N-end rule pathway, contrary to expectations. See FIG. 6C. FIG. 6A shows that Rad23-HA is unstable in ubc4Δ ubcΔ indicating that these E2 proteins do not affect its stability. The degradation of Rad23-HA was also unaffected in ubc2Δ (FIG. 6B), a strain lacking the ubiquitin-conjugating enzyme essential for this proteolytic system. The stability of Gα (and other substrates of the ubiquitin pathway) was unaffected in rad23Δ or when Rad23 was overexpressed, demonstrating that Rad23-mediated suppression of N-end rule toxicity does not involve the mating response. Unexpectedly, it was discovered that rad23Δ also suppressed the toxic effects of N-end rule overexpression, providing genetic evidence for a connection between Rad23 and the proteolytic system (FIG. 5A).

Figure 7A:
FIGS. 7A-7D are gels showing the growth-stage specific degradation of Rad23-HA.

Rad23-HA is Conditionally Degraded. The data demonstrate that the stability of Rad23-HA varied in a growth-stage-dependent manner. The half-life of Rad23-HA exceeded 1 hour in stationary phase cells and was reduced to approximately 1-3 minutes in actively growing cells (FIG. 7A). Even when overexpressed the half-life of Rad23-HA was approximately 1 minute during active growth, attesting to the extraordinary specificity and potency of the degradation apparatus. To exclude the possibility that overall protein degradation was reduced in stationary-phase cells, thereby causing Rad23-HA stabilization, the stability of two distinct classes of substrates of the ubiquitin pathway was examined. Additionally, the in vivo half-life of Arg-β-gal and Ub-Pro-β-gal (substrates of the N-end rule and UFD pathways, respectively) were measured. See FIG. 7D. Unlike Rad23-HA, Arg-β-gal and Ub-Pro-β-gal were efficiently degraded in both exponential and stationary-phases of growth. In contrast Met-β-gal, which is not recognized as a substrate of the ubiquitin pathway, remained stable in both growth conditions. These results demonstrate that the growth-stage specific degradation of Rad23-HA (and UbL$^{R23}$-β-gal, described in FIG. 9B) is highly specific, and is not a reflection of the overall levels of proteolysis.

Figure 7B:
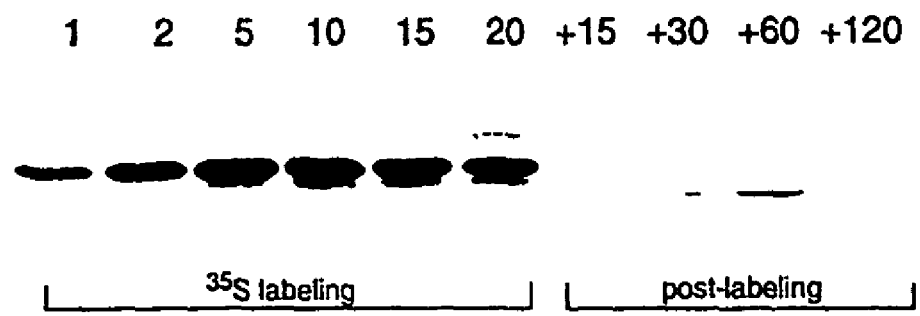

To further characterize the conditions that promote Rad23-HA degradation, stationary-phase yeast cells were radiolabeled to generate high levels of stable Rad23-HA. Rad23-HA was rapidly degraded when these cells were transferred to rich (YPD) medium, and was undetectable within 15 minutes (FIG. 7B). The levels of other proteins were not affected until 60 minutes after transfer. The rapid degradation of Rad23-HA precluded the ability to detect multi-ubiquitinated intermediates.

Figure 7C:
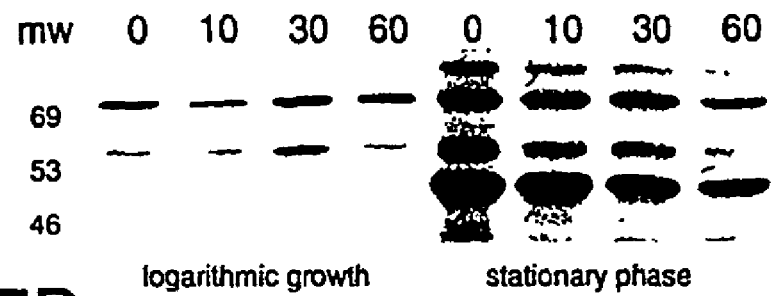
Figure 7D:
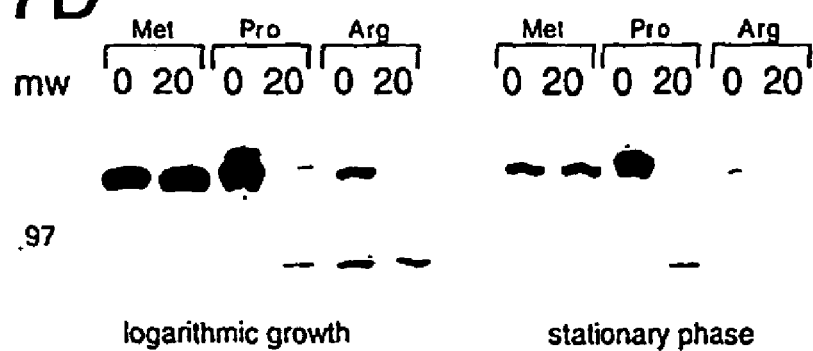
Figure 9A:
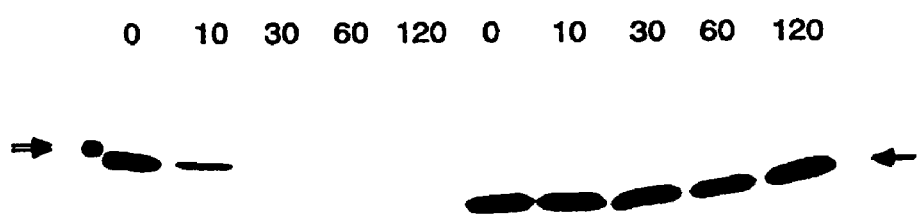
FIGS. 9A and 9B are gels showing that $UbL^{R23}$ is a regulated and portable degradation signal.
Figure 9B:
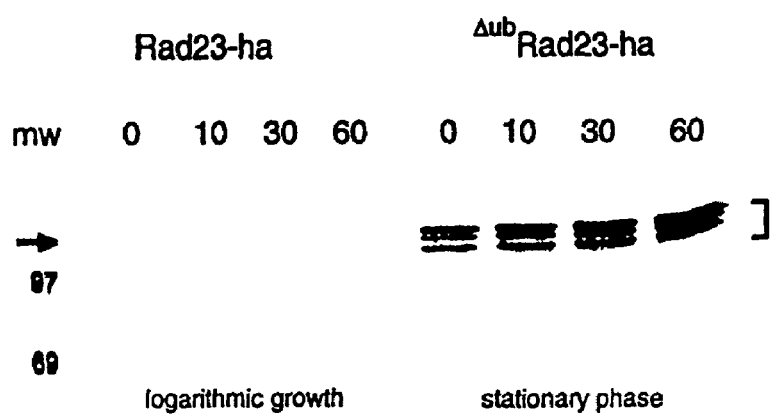

The C-terminal HA epitope does not contribute directly to the destabilization of Rad23-HA because other perturbations of the C-terminus also caused conditional degradation. A Rad23 mutant that lacked 29 C-terminal residues as well as the HA epitope (Rad23$^{1-369}$), displayed extreme instability in logarithmic-phase cells (FIG. 7C), resembling the degradation pattern of both Rad23-HA and UbL$^{R23}$-β-gal (FIG. 9B). Significantly, Rad23$^{1-369}$ conferred UV resistance in rad23Δ, indicating that the function of Rad23 in mediating protein degradation is restricted to stationary-phase cells.

Figure 8A:
FIGS. 8A-8C are gels showing that transient growth-arrest does not affect Rad23-HA stability. The growth of exponential stage cells was arrested and Rad23-HA stability was measured.
Figure 8B:
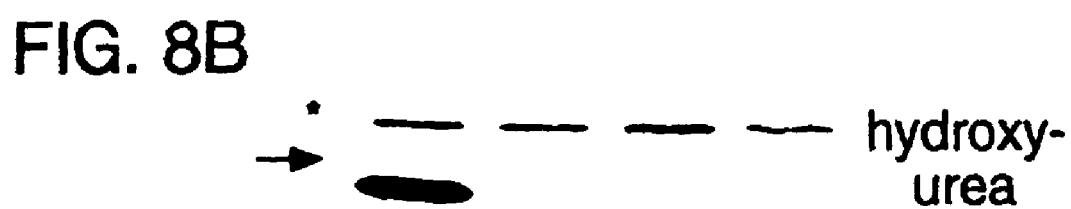
Figure 8C:
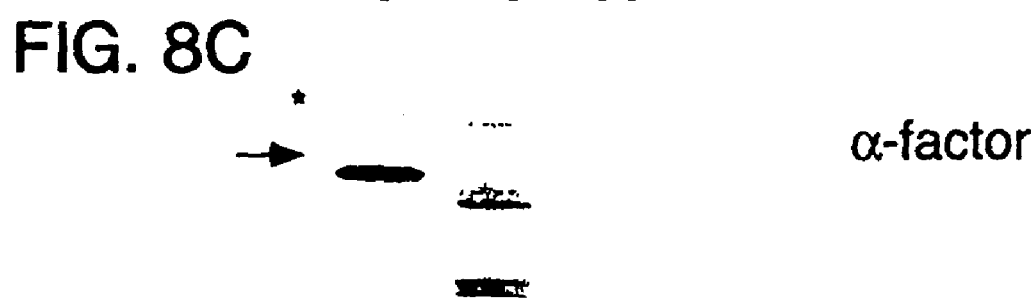

Transient Cell-cycle Arrest Does Not Affect Rad23-HA Stability. The growth-stage-dependent degradation of Rad23-HA prompted the examination of its stability during the cell-cycle. The growth of exponential stage cultures was transiently arrested with α-factor (Madura and Prakash, (1990) supra) or hydroxyurea (Sanchez, et al. (1996) Science 271: 357-360), and Rad23-HA stability was determined. Pulse-chase studies revealed that Rad23-HA was efficiently degraded in these growth-arrested cells (FIGS. 8B and 8C). Also a temperature-sensitive allele of RNA Pol II was employed to asynchronously arrest growth of an actively propagating culture (Nonet, et al. (1987) Mol. Cell. Biol. 7:1602-1613). The data show that Rad23-HA remained extremely short-lived (FIG. 8A). It was therefore concluded from these results that the degradation of Rad23-HA is not affected by transient growth arrest of exponential-phase or proliferative cells and that UbL domain of proteins such as Rad23 are useful in determining the overall or steady-state growth state of a cell. Accordingly, cells which are phenotypically or genotypically predisposed to be proliferative are detectable using a UbL domain of the present invention, even under transient growth arrest.

The Ubiquitin-Like Domain is Required for Rad23-HA Degradation. Ubiquitin is expressed either as an N-terminal fusion to specific ribosomal proteins (Finley, et al. (1989) Nature 338:394-401), or as a chain of tandemly-linked Ub multimers (Ozkaynak, et al. (1990) EMBO J. 6:1429-1439). The C-terminus of Ub is important for its processing, activation and conjugation to cellular proteins. The C-terminal residues in most ubiquitin-like domains differ from that of Ub indicating that they are generally not excised and conjugated to other proteins.

Varshavsky and colleagues found that the expression of Ub as a non-cleavable extension on β-galactosidase led to extreme instability of the fusion protein following subsequent conjugation to a multi-ubiquitin chain (Johnson, et al. (1992) EMBO J. 11:497-505). Since UbL$^{R23}$ is retained in mature Rad23, its role in Rad23-HA degradation was investigated by constructing a mutant that lacked this motif ($^{\Delta UbL}$Rad23-HA). It was found that $^{\Delta UbL}$Rad23-HA was stable in actively growing cells (FIG. 9A), displaying a half-life that exceeded 10 hours during exponential growth. Significantly, $^{\Delta UbL}$Rad23-HA failed to complement the UV sensitivity of rad23Δ (Watkins, et al. (1993) supra), indicating that UbL$^{R23}$ has a proteolytic function in DNA repair.

The Ubiquitin-Like Domain is an Autonomous Degradation Signal. The ability of UbL$^{R23}$ to promote the degradation of a reporter protein was tested by linking it to β-galactosidase (UbL$^{R23}$-β-gal). The data illustrate that UbL$^{R23}$-β-gal is stable in stationary-phase (i.e., quiescent cells) but exceedingly unstable during active growth (i.e. proliferative growth) (FIG. 9A and FIG. 9B), intensifying the degradation pattern of Rad23-HA (FIG. 7A). Long over-exposures of the autoradiograms revealed a low level of UbL$^{R23}$-β-gal signal in the 0 minute sample in logarithmically growing cells, and quantitative β-galactosidase activity measurements confirmed these findings. These results demonstrate that UbL$^{R23}$ is both necessary and sufficient for the targeting and degradation of Rad23-HA, and contains amino acid residues that are recognized by proteolytic factors. Furthermore, UbL$^{R23}$ contains sequences that are sensitive to regulatory signals because UbL$^{R23}$-β-gal mimicked the regulated degradation of Rad23-HA. UbL$^{R23}$-β-gal migrated as a set of three closely spaced electrophoretic bands. It was not determined if these bands correspond to multiubiquitination or other modifications of UbL$^{R23}$-β-gal. However, these data further demonstrate the use of an UbL domain for detecting a proliferative cell with a catalytically active 26S proteasome.

The Ubiquitin Fusion Degradation (UFD) Pathway is Involved in the Degradation of Rad23-HA. The placement of ubiquitin on the N-terminus of a protein such as β-galactosidase (Ub-Pro-β-gal), promotes degradation by the Ubc4 ubiquitin-conjugating enzyme (Bachmair, et al. (1986) Science 234:179-186). Ubc4 assembles a multiubiquitin chain at a conserved lysine in the Ub extension of Ub-Pro-β-gal (Johnson, et al. (1992) supra). Since the lysine residues which serve as attachment sites for the formation of a multiubiquitin chain are conserved between Ub and UbL$^{R23}$ (see FIG. 19A), it was expected that Rad23-HA might also be targeted by Ubc4. Ubc5 encodes another ubiquitin-conjugating enzyme which is approximately 90% identical to Ubc4 and is believed to have overlapping substrate specificity (Seufert and Jentsch (1990) EMBO J. 9:543-550). Rad23-HA stability was examined in ubc4Δ ubc5Δ. In these cells, degradation of the protein was unaffected (FIG. 6A) compared to the wild-type strain. These findings show that this class of E2 enzymes does not target Rad23-HA for degradation.

Figure 10A:
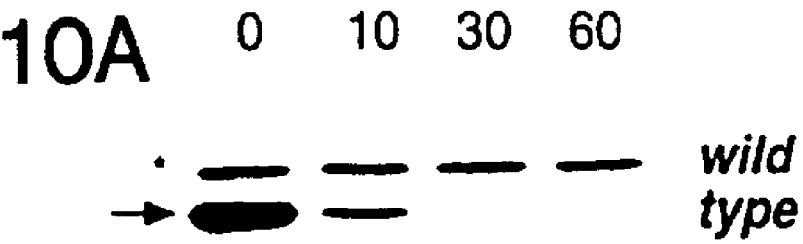
FIGS. 10A-10E show that Ufd5 is required for the degradation of Rad23-HA. Rad23-HA was expressed in a set of strains bearing mutations in ufd1-5. In vivo stability was measured by pulse-chase methods and quantitated by PHOSPHORIMAGER. Only ufd5Δ was found to be important for Rad23-HA degradation. An antibody cross-reacting band (*) served as a useful internal control for loading
Figure 10B:
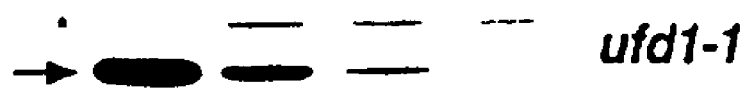
Figure 10C:
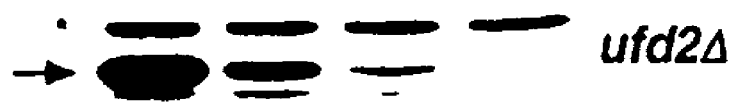
Figure 10D:
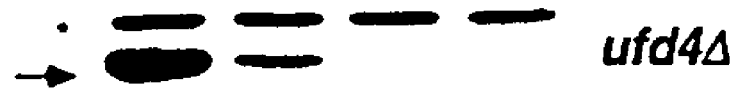
Figure 10E:
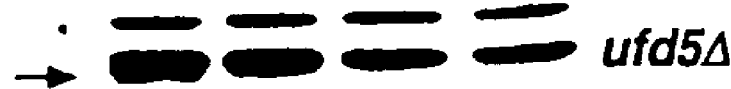

In a search for factors that affect the degradation of Ub-Pro-β-gal Johnson, et al. performed a genetic screen and identified a class of mutants (termed the UFD pathway, for ubiquitin fusion degradation pathway) that differentially affected Ub-Pro-β-gal stability. Johnson et al. determined that UFD5 was the only UFD pathway gene that was also required for the degradation of N-end rule substrates, which are distinct from Ub-Pro-β-gal. While N-end rule substrates are ubiquitinated by Ubc2 and Ubr1, Ub-Pro-β-gal is ubiquitinated by Ubc4. The possibility that the ufd mutants might affect the stability of Rad23-HA was examined. Pulse-chase measurements showed that Rad23-HA was strongly stabilized in ufd5Δ (FIG. 10E), but not in ufd1-ufd4 (FIGS. 10B-10D). Multiubiquitinated derivatives of Ub-Pro-β-gal were detected in ufd5Δ, while Rad23-HA accumulated as an apparently unmodified protein. These results demonstrate that the channeling of substrates to the proteasome can follow diverse routes. This observation is also supported by the finding that different proteasome mutants have distinct effects on Rad23-HA stability.

Figure 11A:
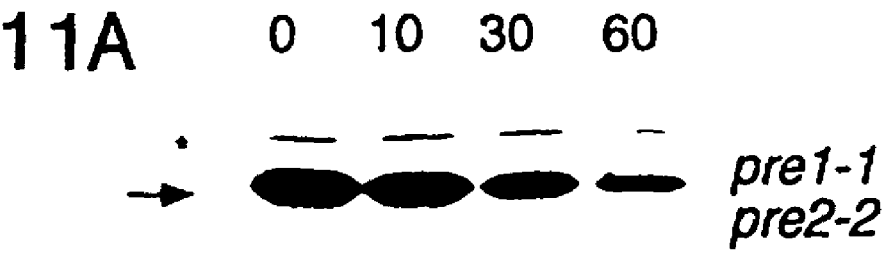
FIGS. 11A-11E are a series of gels showing that Rad23-HA is degraded by the proteasome. The in vivo stability of Rad23-HA in proteasome and vacuolar mutant strains is shown.
Figure 11B:

Proteasome Dependent Degradation of Rad23-HA. Substrates of the Ub system are generally degraded by the 26S proteasome, an evolutionarily conserved structure of >2×10$^6$ Daltons. It has been reported that a yeast pheromone-specific receptor, Ste2, is ubiquitinated but degraded in the vacuole in a proteasome-independent manner (Hicke and Riezman (1996) Cell 84:277-287). In contrast, ornithine decarboxylase (ODC) is degraded by the 26S proteasome, although it is not ubiquitinated (Tokunage, et al. (1994) J. Biol. Chem. 269:17382-17385). Given these exceptions to the generally accepted model for targeting and degradation of ubiquitinated substrates, the stability of Rad23-HA in yeast strains bearing mutations in either proteasome subunits or vacuolar proteases was measured to determine if its degradation involved the ubiquitin/proteasome pathway. Cim5 is an ATPase subunit of the 19S regulatory complex of the 26S proteasome and is required for the degradation of Ub-Pro-β- gal (Ghislain, et al. (1993) *Nature* 366:358-361). Cim5-1 mutant cells are conditional mutants that arrest the cell cycle at non-permissive temperature and accumulate ubiquitinated proteins (Schork, et al. (1995) *J. Biol. Chem.* 270:26446-26450). The stability of Rad23-HA in exponential-stage cim5-1 cells was measured and the results show that it was very stable ($t_{1/2}$>10 hours, FIG. 11B). Pre1 and Pre2 are subunits of the 20S catalytic core of the 26S proteasome, and conditional mutants of these subunits grow poorly under standard conditions and are sporulation-defective and stress-sensitive. In agreement with the results observed in cim5-1, it was found that Rad23-HA was stabilized in actively growing pre1-1 pre2-2 cells ($t_{1/2}$-1 hour, FIG. 11A). In contrast, the degradation Rad23-HA was unaffected in pep4Δ prb1-Δ1, which is defective in vacuolar proteolysis (Hicke and Riezman (1996) supra). See FIG. 11E. Thus, it appears that Rad23-HA degradation requires the 26S proteasome.

Figure 11C:
Figure 11D:
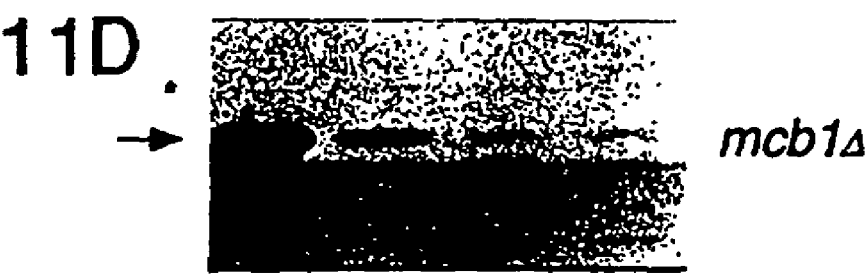
Figure 11E:
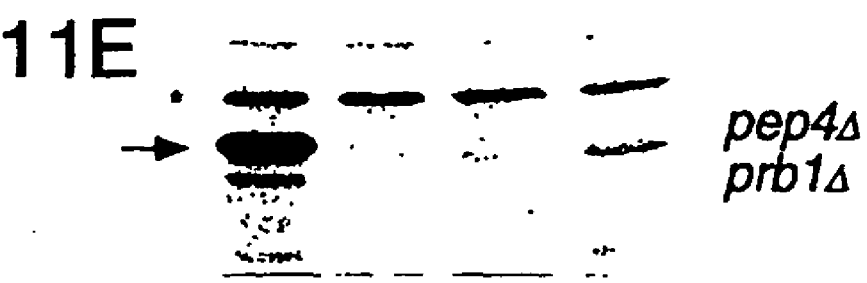

The very rapid degradation of Rad23-HA precluded detection of multiubiquitin intermediates. Ubiquitinated Rad23 was previously detected (Watkins, et al. (1993) supra), indicating that Rad23-HA degradation is ubiquitin-mediated. Mcb1 is a yeast counterpart of the human S5a protein which encodes. a multiubiquitin-chain binding protein of the 26S proteasome. The stability of Rad23-HA was tested in mcb1Δ and results demonstrated that it continued to be degraded rapidly (FIG. 11D). Since mcb1Δ stabilizes only a subset of ubiquitinated substrates in yeast cells it is possible that other multiubiquitin-chain binding proteins can mediate Rad23-HA degradation. The stability of Rad23-HA in doa4Δ-1, an isopeptidase associated with the 26S proteasome, was also measured since many substrates of the ubiquitin system are stabilized in this mutant. Unexpectedly, Rad23-HA continued to be degraded in doa4Δ-1 (FIG. 11C). These results demonstrate that substrates of the ubiquitin system can follow diverse routes into the proteasome.

Rad23 Interacts with Other Components of the Proteasome. Rad23 was linked to lexA and interacting factors were sought by the 2-hybrid method (Paetkau, et al. (1994) *Genes & Dev.* 8:2035-2045). Irt1 (interaction with Rad23), a protein whose C-terminal domain displays significant homology with the 26S subunit Yta6 (FIG. 8A), Cim3 and Cim5 was identified in this screen. See FIG. 12A. The large N-terminal domain of Irt1 is not similar to any known polypeptide sequence. The degradation of Rad23-HA was unaffected in irt1Δ, indicating that the interaction between Rad23 and Irt1 is likely to be of a regulatory nature.

Figure 12B:
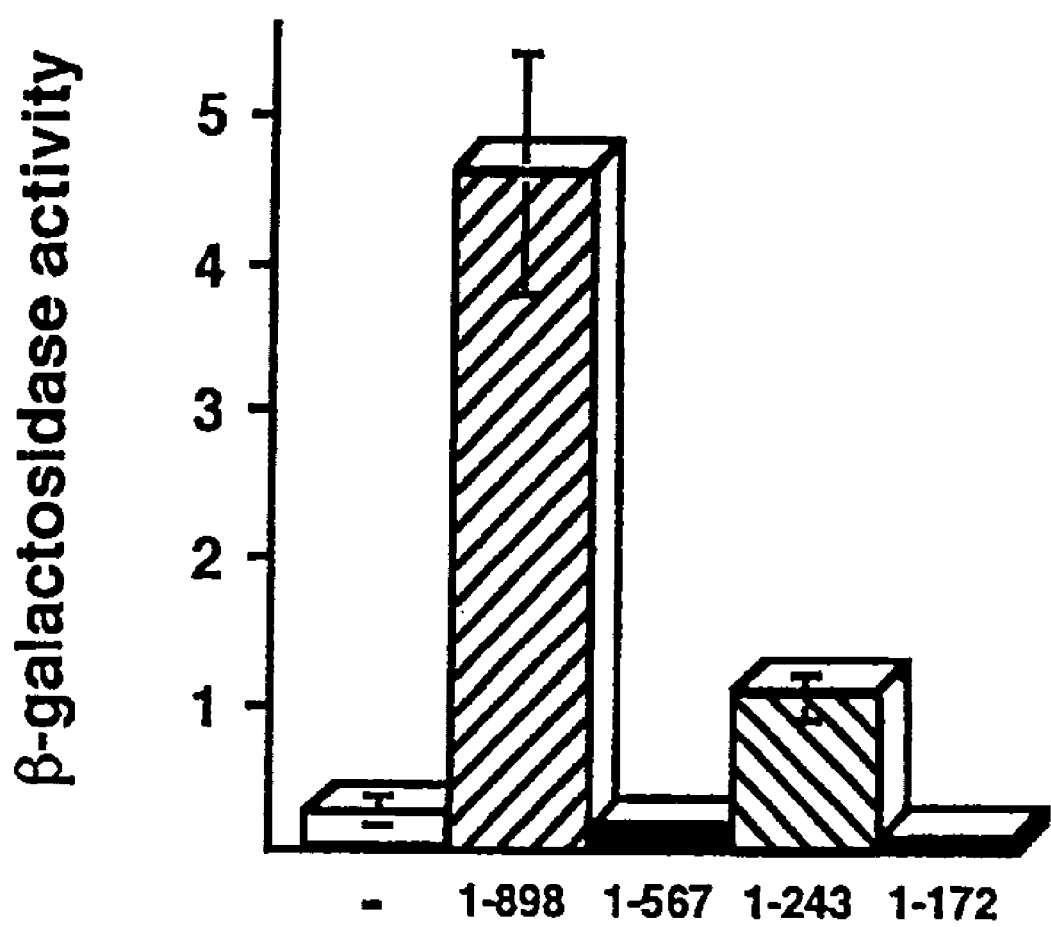

To further characterize the interaction between Rad23 and Irt1, several deletion derivatives of Irt1 were constructed and tested for their ability to interact with Rad23 (FIG. 12B). Full-length Irt1 (897 amino acids) as well as three C-terminal deletion variants, containing residues 1-567, 1-243 and 1-172, were tested in the 2-hybrid system. Irt1$^{1-567}$ lacks the highly conserved ATPase domain located in the C-terminus, while the larger truncations removed additional residues of unknown function.

Example 3

Ubiquitin-Like Sequences are Proteasome Interacting Domains

A family of proteins that contain ubiquitin-like sequences (UbL's) has been identified in diverse organisms (Garrett, et al. (1995) *Proc. Natl. Acad. Sci. USA* 92:7172-7176; Shen, et al. (1996) *Genomics* 36:271-279). Some UbL's are post-translationally conjugated to other proteins in a mechanism similar to that described for ubiquitin-conjugation (Johnson, et al. (1997) *J. Biol. Chem.* 272:26799-26802; Mahajan, et al. (1997) *Cell* 88:97-107). However, a distinct class of UbL's are retained in the original translational product and not conjugated to other proteins (Watkins, et al. (1993) supra). The proteins to which these UbL's are fused share little in common and offer no obvious clues to their biological functions. Furthermore, the effect of an UbL on the activities of the protein to which it is linked is unknown. Although UbL's display no more than 20-30% identity to the amino acid sequence of ubiquitin, there are conserved regions amongst the domains (e.g., SEQ ID NO:1 and SEQ ID NO:2) and their 3-dimensional structures are predicted to be highly similar (van der Spek, et al. (1996) *Genomics* 31:20-27). The two proteins in yeast that contain N-terminal ubiquitin-like domains were reported to be stable (Biggins, et al. (1996) *J. Cell Biol.* 133:1331-1346). However, it has now been determined that Rad23 is ubiquitinated and degraded during the G1/S-phase transition of the cell-cycle. The fusion of ubiquitin to the N-terminus of β-galactosidase (Ub-Pro-β-gal) has also been shown to cause rapid degradation by the ubiquitin pathway (Johnson, et al. (1995) *J. Biol. Chem.* 270:17442-17456; Bachmair, et al. (1986) *Science* 234:179-186).

Dsk2 is another yeast protein that contains a ubiquitin-like domain (UbL$^{DSK}$), and deletion of both genes (rad23 dsk2) causes a temperature-sensitive growth defect, indicating that their activities converge at some unknown biochemical level.

To examine if Rad23 associated with proteolytic factors, Rad23 and UbL$^{R23}$ were operably linked to GST and it was found that both GST-Rad23 and GST-UbL$^{R23}$ formed stable interactions with the 26S proteasome. See Example 1. The data presented herein demonstrate that proteasome-interaction is a feature shared by other members of the family of ubiquitin-like proteins, and indicate that UbL domain containing proteins mediate proteolytic functions. UbL's and UbL domain-containing proteins have been implicated in many biological pathways including DNA repair (Watkins, et al. (1993) supra), spindle pole-body duplication (Biggins, et al. (1996) supra), transcription elongation (Garrett, et al. (1995) supra), von Hipple Landau syndrome (Kibel, et al. (1995) supra) and nuclear/RNA transport (Mahajan, et al. (1997) supra). The best characterized among these proteins is yeast Rad23.

The findings presented herein indicate that UbL/proteasome interaction is regulated. The UbL from yeast Dsk2 (UbL$^{DSK}$) interacts with the proteasome preferentially in actively growing cells. Overexpression of UbL$^{R23}$ inhibits the degradation of specific substrates of the ubiquitin pathway perhaps by saturating the proteasome targeting pathway. Significantly, these results show that UbL-linked proteins interact with the proteasome without prior attachment to a multiubiquitin chain, defining a novel mechanism for targeting proteins to the proteasome.

Strains and Extracts. The yeast strains used in these studies were derived from JD47-13C (MATa his3-Δ200 trp1Δ63 lys2-801 ura3-52 leu2-2, 112). Rad23 deletion (CSY85; rad23Δ::URA3) was made in JD47-13C using pDG28. Extracts for immunoprecipitations and affinity purified purification were according to standard methods.

Reagents. Proteasome inhibitors were obtained from CALBIOCHEM, glutahione-SEPHAROSE from PHARMACIA, anti-ubiquitin antibodies from SIGMA, and anti-β-galactosidase antibodies from PROMEGA.

Plasmids and Constructs. UBL's and CIM5 were amplified by PCR with oligonucleotides containing a 5' NcoI and 3' KpnI restriction site and ligated into similarly treated pCBGST1. The expression of the proteins was induced with 0.15 mM $CuSO_4$. Plasmids encoding Pre-1-FLAG and Sen3-HA are known in the art.

Figure 13A:
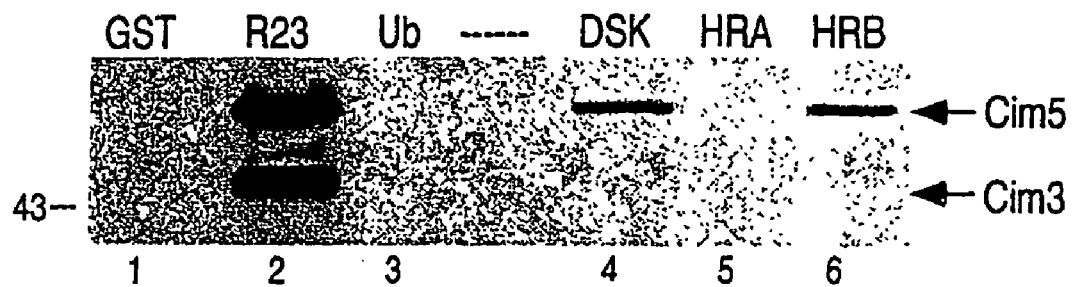
FIGS. 13A and 13B are gels showing that UbL's from different sources interact with the proteasome. GST linked proteins were expressed in yeast and purified on glutathione-SEPHAROSE. Proteins retained on the beads were resolved in SDS-polyacrylamide gels, transferred to nitrocellulose, and incubated with antisera specific to proteasome subunits Cim3 and Cim5. The blot was developed by enhanced chemiluminescence (AMERSHAM).
Figure 14A:
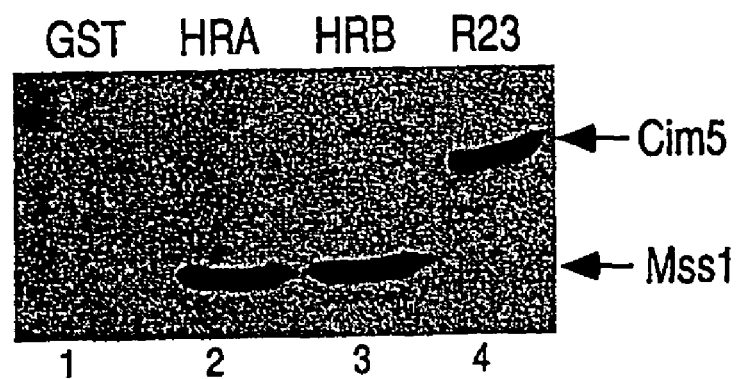
FIGS. 14A and 14B are a series of blots showing that UbL's interact with the 19S/PA700 complex.

UbL's are Proteasome-Interacting Sequences. The ubiquitin-like domains of yeast Rad23 and Dsk2, and human HHR23A (HRA) and HHR23B (HRB), were linked to the C-terminus of glutathione S-transferase (GST), and expressed in yeast. Extracts were incubated with glutathione-SEPHAROSE, and bound proteins separated in a SDS-polyacrylamide gel, transferred to nitrocellulose and analyzed by immunological methods. The blot was incubated with Cim3 and Cim5 antibodies, which recognize subunits of the 26S proteasome, and a strong interaction was detected in the beads containing GST-$UbL^{R23}$. See FIG. 13A, lane 2. $UbL^{R23}$/proteasome interaction was resistant to 1M NaCl, and treatment with detergents including 1% TRITON X-100, 0.5% NP40 and 0.1% SDS. Ubiquitin (GST-Ub) did not interact appreciably with the 26S proteasome (FIG. 13A, lane 3), indicating that ubiquitin is recognized by the proteasome only when it is assembled into a multiubiquitin chain (Chau, et al. (1989) *Science* 243:1576-1583). In contrast, the UbL may have evolved to specifically interact with the proteasome without prior attachment to a multiubiquitin chain. Weaker interactions were detected with GST-$UbL^{DSK}$ and GST-$UbL^{HRB}$ (lanes 4 and 6), but not with GST-$UbL^{HRA}$ (lane 5). To determine whether GST-$UbL^{HRA}$ and GST-$UbL^{HRB}$ might interact more favorably with human proteins, Hela cell S100 extracts were incubated with GST-$UbL^{HRA}$ and GST-$UbL^{HRB}$. The interacting proteins were analyzed via western blot analysis with Cim5 antibodies which cross-react with Mss1, a human counterpart of yeast Cim5 (Ghislain, et al. (1993) *Nature* 366:358-361). Mss1 was detected in GST-$UbL^{HRA}$ and GST-$UbL^{HRB}$ beads (FIG. 14A, lanes 2 and 3), but not GST (lane 1). A control lane containing GST-$UbL^{R23}$ interacting proteins showed that the antibody reaction against Cim5 was efficient (FIG. 14A, lane 4). In agreement with these findings it was found that cells expressing Sen3-HA, a non-ATPase 19S subunit (DeMarini, et al. (1995) *Mol. Cell. Biol.* 15:6311-21), also interacted with GST-$UbL^{R23}$ but not GST (see FIG. 14A).

Figure 13B:
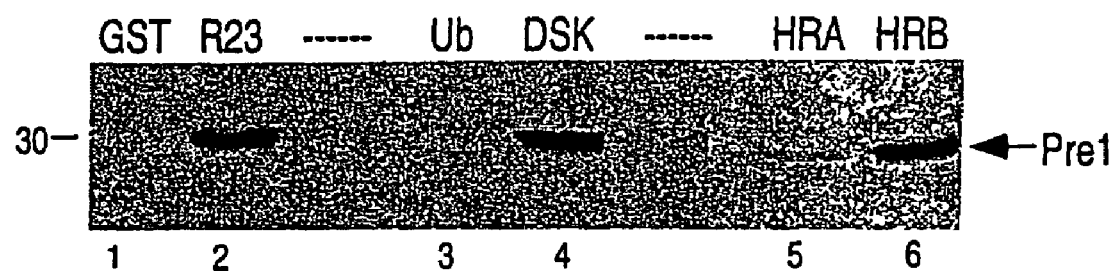

Consistent with these results, Pre1-FLAG (an epitope-tagged 20S subunit) was detected in beads containing GST-$UbL^{R23}$, GST-$UbL^{DSK}$, and GST-$UbL^{HRB}$ (FIG. 13B). These results show that several different subunits of the 19S and 20S components of the 26S proteasome can be detected in a complex that interacts with ubiquitin-like domains. It is concluded that a common biochemical property of UbL domains disclosed herein is the interaction with catalytically active 26S proteasome.

Figure 14B:
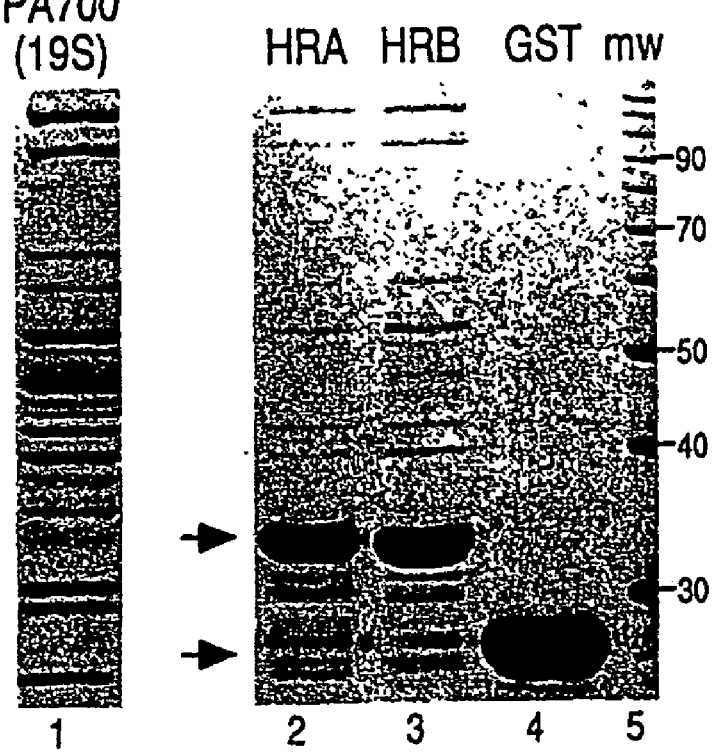

UbL's Interact with the 19S Regulatory Component of the 26S Proteasome. Based on the activities associated with $UbL^{R23}$, the proteasome interacting-subunit could be located in either the 19S or 20S complexes. To examine the interaction with the 19S regulatory complex GST-$UbL^{HRA}$ and GST-$UbL^{HRB}$ were incubated with approximately 5 μg 19S/PA700 for 10 hours at 4° C. Bound proteins were resolved in SDS-PAGE and examined by silver staining. A significant fraction of the input protein was detected in the beads containing $UbL^{HRA}$ and $UbL^{HRB}$ (FIG. 14B, lanes 2 and 3). The profile of 19S/PA700 subunits that bound GST-$UbL^{HRA}$ and GST-$UbL^{HRB}$ was similar demonstrating that the entire complex, rather than specific subunits, interacts with the UbL. $UbL^{HRB}$, but not $UbL^{HRA}$, showed detectable interaction with yeast proteasomes, although both chimeras bound human proteasome (FIG. 14). This variance in interaction may result from subtle differences in their sequences, which might offer clues to the residues that are important for proteasome binding.

A novel mechanism is involved in $UbL^{R23}$/proteasome interaction. Substrates of the ubiquitin system are covalently linked to a multiubiquitin chain prior to recognition by the 26S proteasome. In a search for multiubiquitin-chain binding proteins Mcb1, which is a component of the 19S regulatory complex of the proteasome was identified (van Nocker, et al. (1996) *Mol. Cell. Biol.* 16:6020-6028). Since UbL's interact with the proteasome through the 19S complex (FIG. 14B), it was determined whether $UbL^{R23}$ could interact with the proteasome in mcb1Δ. GST-$UbL^{R23}$ was purified from mcb1Δ and it was found that it co-precipitated Cim5 and Cim3, demonstrating that its interaction with the proteasome is not mediated by Mcb1. This result demonstrates that there are alternate ways for substrates and regulators to interact with the proteasome, and is consistent with studies which showed that some substrates of the ubiquitin system are efficiently degraded in mcb1Δ (van Nocker, et al. (1996) supra).

Figure 15:
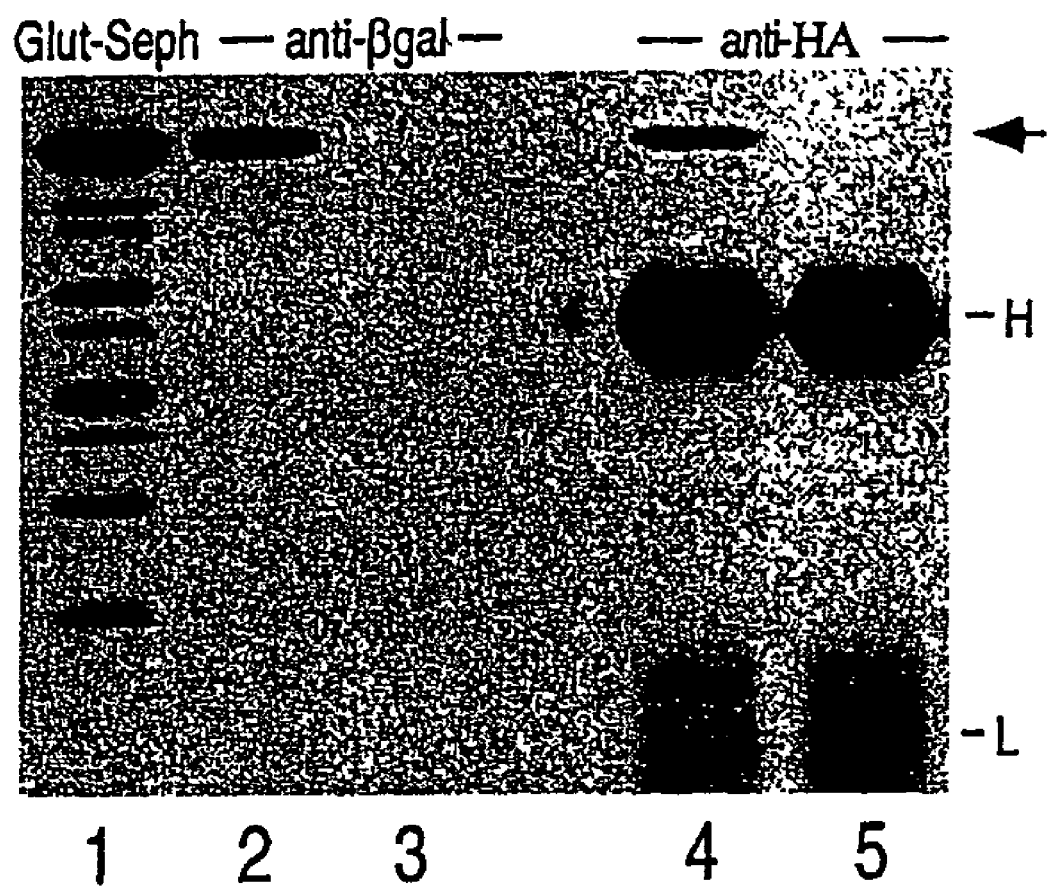
FIG. 15 is a gel showing that $UbL^{R23}$ can target heterologous proteins to the proteasome. $UbL^{R23}$ was linked to β-galactosidase and Ura3-HA and transformed into yeast cells expressing GST-Cim5. Lane 1 contains affinity purified GST-Cim5. $UbL^{R23}$-βgal was immunopurified with anti-β-galactosidase antibodies and GST-Cim5 was co-purified (lane 2). An extract containing only GST-Cim5 was treated with anti-β-galactosidase antibodies (lane 3). $UbL^{R23}$-Ura3-HA was precipitated with anti-HA antibodies and GST-Cim5 was co-purified (lane 4). An extract containing only GST-Cim5 was incubated with anti-HA antibodies and resolved as a negative control (lane 5). The blot was developed with anti-GST antibodies. (H and L indicate the positions of immunoglobulin heavy- and light-chains from the HA immunoprecipitation).

UbLR23 can Target Heterologous Proteins to the Proteasome. $UbL^{R23}$ was linked to the N-terminus of β-galactosidase ($UbL^{R23}$-β-gal) and Ura3-HA ($UbL^{R23}$-Ura3-HA), and the plasmids were transformed into a yeast strain expressing GST-Cim5. Extracts were incubated with anti-β-galactosidase or anti-HA antibodies, and immunoprecipitated protein recovered on Protein-A SEPHAROSE beads, resolved in SDS-PAGE and transferred to nitrocellulose. The nitrocellulose filter was incubated with anti-GST antibodies, and the position of full-length GST-Cim5 from a control extract was identified (arrow in FIG. 15, lane 1). GST-Cim5 was found to be highly susceptible to proteolysis (as indicated by the large number of smaller fragments). Extracts containing GST-Cim5 and $UbL^{R23}$-β-gal were incubated with anti-β-galactosidase, and a strong reaction against GST-Cim5 was detected in the immunoprecipitates (FIG. 15, lane 2). Unexpectedly, the degradation products of GST-Cim5 (lane 1) were not seen in lane 2, indicating that only intact GST-Cim5 was incorporated into the proteasome. Extracts containing only GST-Cim5 were also incubated with anti-β-galactosidase antibodies and resolved on the gel. As expected, GST-Cim5 was not precipitated in this reaction (FIG. 15, lane 3). To extend these findings further, it was determine whether $UbL^{R23}$-Ura3-HA could also selectively precipitate GST-Cim5. A band consistent with GST-Cim5 was detected (lane 4), and as observed in lane 3 only intacting GST-Cim5 protein was precipitated with $UbL^{R23}$-Ura3-HA. An extract containing only GST-Cim5 was reacted with anti-HA antibodies and GST-Cim5 was not precipitated (lane 5). It was concluded that $UbL^{R23}$ was an autonomous sequence that could target unrelated proteins to the proteasome UBL/PROTEASOME INTERACTION CAN BE regulated. It was found that $UbL^{DSK}$ forms a weak association with the proteasome. The function of Dsk2 is expected to be confined to actively growing cells because it is required for spindle pole-body duplication. These studies indicate that $UbL^{DSK}$ interacts more favorably with the proteasome in actively growing cells. Example 1 discloses that specific alleles of Rad23 are rapidly degraded by the ubiquitin/proteasome pathway, in a mechanism that requires $UbL^{R23}$. Since these Rad23 variants are degraded only in actively growing cells, it appears that $UbL^{R23}$/proteasome interaction may also be regulated.

Figure 16A:
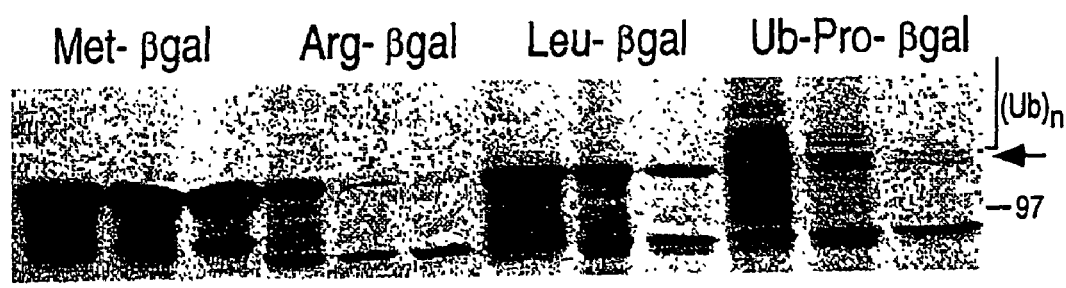
FIGS. 16A and 16B are a pair of gels illustrating that $UbL^{R23}$ interferes with the degradation of specific substrates. Yeast cells expressing a test protein Met-β-gal, or substrates of the N-end rule (Arg-β-gal and Leu-β-gal) and UFD pathway (Ub-Pro-β-gal) were transformed with plasmids expressing GST or GST-$UbL^{R23}$. The stability of the proteins was determined by $^{35}$S-pulse-chase methods. Samples were analyzed after 0, 10 and 60 minutes in Chase medium containing cycloheximide. The precipitated proteins were separated by SDS-PAGE and the fluorograms exposed to X-ray film. This figure reproduces a dark exposure of the gel to reveal high molecular-weight derivatives of Leu-β-gal and Ub-Pro-β-gal (indicated as (Ub)n) in cells expressing GST-$UbL^{R23}$.
Figure 16B:
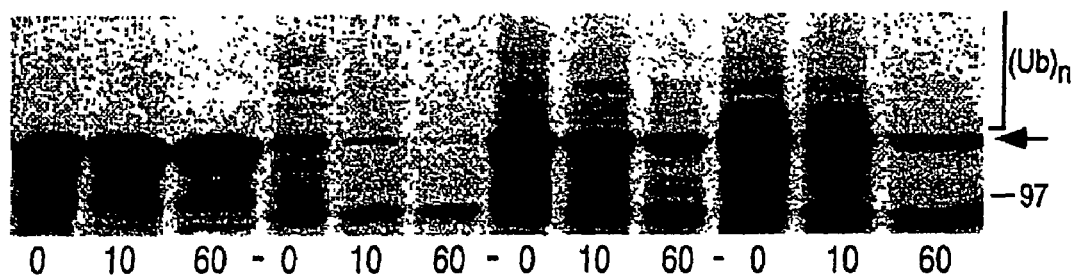

$UbL^{R23}$ Interferes with Proteasome Function. The high affinity interaction between $UbL^{R23}$ and the 26S proteasome indicated that it might affect the degradation of substrates of the ubiquitin system. The stability of substrates of the N-end rule (Arg-β-gal and Leu-β-gal) and UFD pathways (Ub-Pro-β-gal) were examined by measuring β-galactosidase activity of test substrates. The levels of Leu-β-gal and Ub-Pro-β-gal were 2-3 fold higher in cells expressing GST-UbL$^{R23}$, than in the GST control. In contrast, the activity in cells expressing Met-β-gal and Arg-β-gal was unchanged. To confirm these results, the in vivo half-lives of test substrates were measured by pulse-chase analysis. It was found that Leu-β-gal and Ub-Pro-β-gal were moderately stabilized in cells expressing GST-UbL$^{R23}$ (FIG. 16B), as compared to GST (FIG. 16A). These results are in agreement with the β-galactosidase activity measurements. Significantly, ubiquitinated derivatives of Leu-β-gal and Ub-Pro-β-gal accumulated in cells expressing GST-UbL$^{R23}$, indicating that UbL$^{R23}$ interferes with a post-targeting step in substrate degradation. This effect is most easily seen in Leu-β-gal levels at the 0 time-point. These results indicate that UbL$^{R23}$ interaction with the proteasome can block, or otherwise interfere with, the access of specific substrates to the proteasome. The alternate possibility that GST-UbL$^{R23}$ increased ubiquitin-conjugation is considered less likely because the rate of Leu-β-gal degradation was reduced, and not increased as would be expected if it was more efficiently targeted. In contrast to the stabilization of Leu-β-gal, Arg-β-gal remained extremely unstable in strains expressing either GST or GST-UbL$^{R23}$. This result indicates that the fate of Type I (Arg-β-gal) and Type II (Leu-β-gal) substrates of the N-end rule pathway may diverge following their conjugation to ubiquitin by the targeting components Ubr1/Ubc2.

It is demonstrated herein that the UbL domain is a cis-acting signal that can translocate UbL domain-linked proteins to the proteasome. In addition to the Rad23 proteins and Dsk2, the interaction between Elongin-B and the proteasome was examined. Consistent with the findings shown in FIG. 13, an interaction with Cim5 was detected. Elongin B is a UbL-containing protein that forms a heterotrimeric complex which modulates transcription by RNA Pol II. It has also been reported elsewhere that UbL$^{R23}$ can function as a portable degradation signal, when fused to the N-terminus of β-galactosidase (UbL$^{R23}$-β-gal). The biological significance of UbL/proteasome interaction may be that UbL's can be either substrates or regulators of the proteasome. There also exists the possibility that a UbL-linked protein can promote the degradation of other proteins in trans, by binding and transporting them to the proteasome. A particular advantage of this mechanism for proteasome targeting is that an elaborate ubiquitin-dependent apparatus is dispensed with, and the in vivo levels of a substrate could be regulated by the concentration of its cognate UbL-containing partner, and its affinity for the proteasome. A precedent for this mechanism is noted by the (ubiquitin-independent) antizyme-mediated degradation of ornithine decarboxylase by the proteasome (Murakami, et al. (1992) *Biochem. J.* 283:661-664). A potential target for Rad23-mediated degradation could be Rad4, to which it binds with high affinity. Rad23 and Rad4 are both important for the assembly of the nucleotide excision repair complex, and genetic and biochemical studies have implicated a regulatory role for Rad23. It has now been shown that Rad23 and Rad4 can be purified in a complex with the proteasome, although it remains to be determined if Rad23 influences Rad4 stability. The Rad23-mediated link between DNA repair and protein degradation may define a mechanism to recycle the repair complex, or to facilitate recovery after the completion of DNA repair.

Of the four UbL's present in yeast, only Smt3 and Rub1 are conjugated post-translationally to other proteins. A mammalian counterpart of Smt3 (SUMO) is covalently linked to RanGAP1, although this modification does not appear to promote degradation. However, it is possible that only a small fraction of RanGAP1 is post-translationally modified, and its SUMO-mediated turnover may be masked by the large fraction of unmodified RanGAP1. It is demonstrated in FIG. 13 that mono-ubiquitin (GST-Ub) failed to interact with the proteasome. Since ubiquitin interacts with the proteasome only when it is assembled into a multiubiquitin chain, it is believed that substrate-linked Smt3 and substrate-linked Rub1 might also be targeted to the proteasome.

UbL-containing proteins may prevent the degradation of other proteins by blocking their access to proteolytic factors. For instance, GST-UbL$^{R23}$ interaction with the proteasome inhibited the degradation of specific substrates of the ubiquitin pathway (FIG. 16). It was found that UbL$^{R23}$ stabilized Leu-β-gal but not Arg-β-gal, which are distinct substrates of the N-end rule pathway.

UbL$^{R23}$ also stabilized Ub-Pro-β-gal, a substrate of the UFD pathway. Pulse-chase experiments indicated that inhibition of degradation occurred at a post-targeting step because multi-ubiquitinated derivatives of Leu-β-gal and Ub-Pro-β-gal accumulated in the presence of GST-UbL$^{R23}$.

Rad23 and Dsk2 are yeast proteins that retain ubiquitin-like domains in the mature proteins. Rad23 is required for nucleotide excision repair, while Dsk2 is involved in spindle pole-body (SPB) duplication. Deletion of both genes (rad23 dsk2) causes a temperature-sensitive growth defect indicating that the biochemical activities of Rad23 and Dsk2 intersect, possibly at the level of the 26S proteasome. UbL$^{R23}$, but not UbL$^{DSK}$, interferes with the degradation of specific test proteins. It is believed that substrates of the N-end rule and UFD pathway may be channeled to a specific proteasome isoform that is recognized only by UbL$^{R23}$. Unexpectedly, UbL$^{DSK}$/proteasome interaction is enhanced in actively growing cells, also indicating that compositionally distinct types of proteasomes may regulate UbL interactors. This observation is consistent with a previous study which showed that specific 20S proteasome subunits are replaced following γ-interferon treatment in mammalian cells (Gaczynska, et al. (1993) *Nature* 365:264-267).

Example 4

Enhanced Thermostability of Rad23

Figure 17:
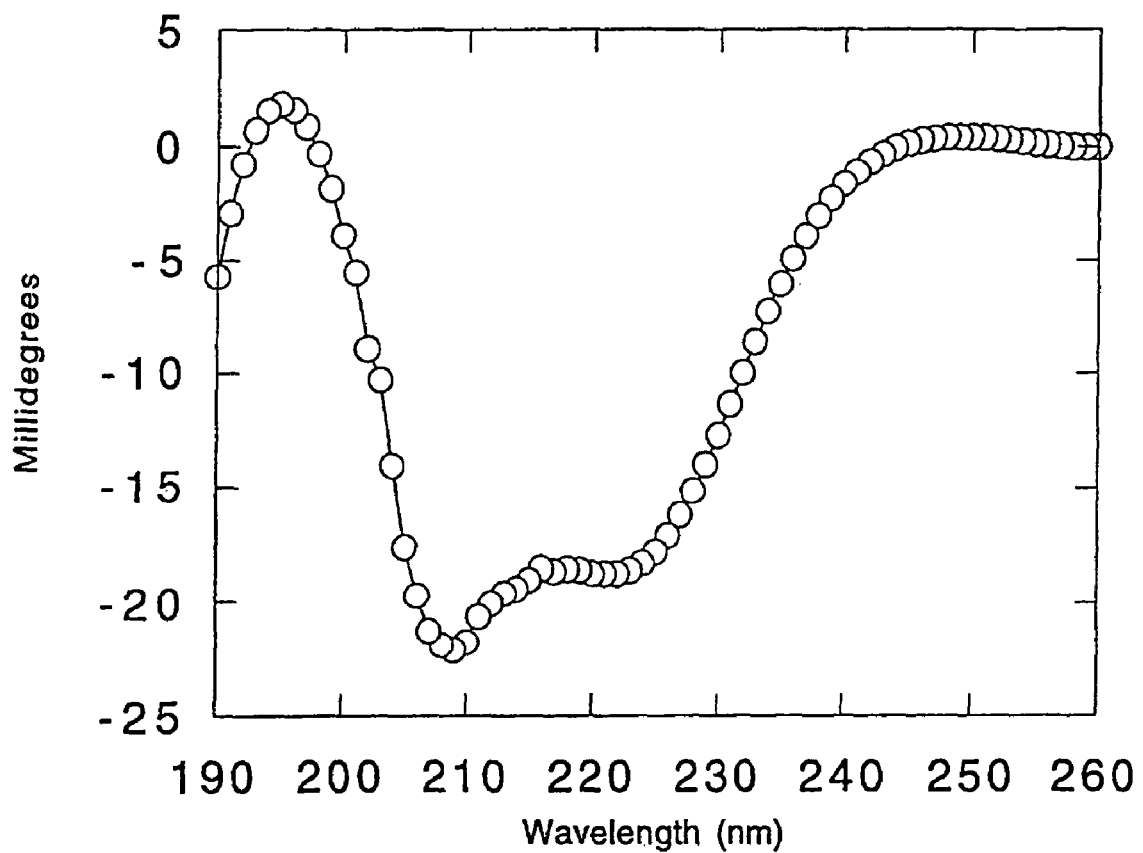
FIG. 17 is a graph showing the CD spectra of Rad23. The data show the spectra of a typical globular protein. The CD spectra of the protein is not altered by heating.
Figure 18:
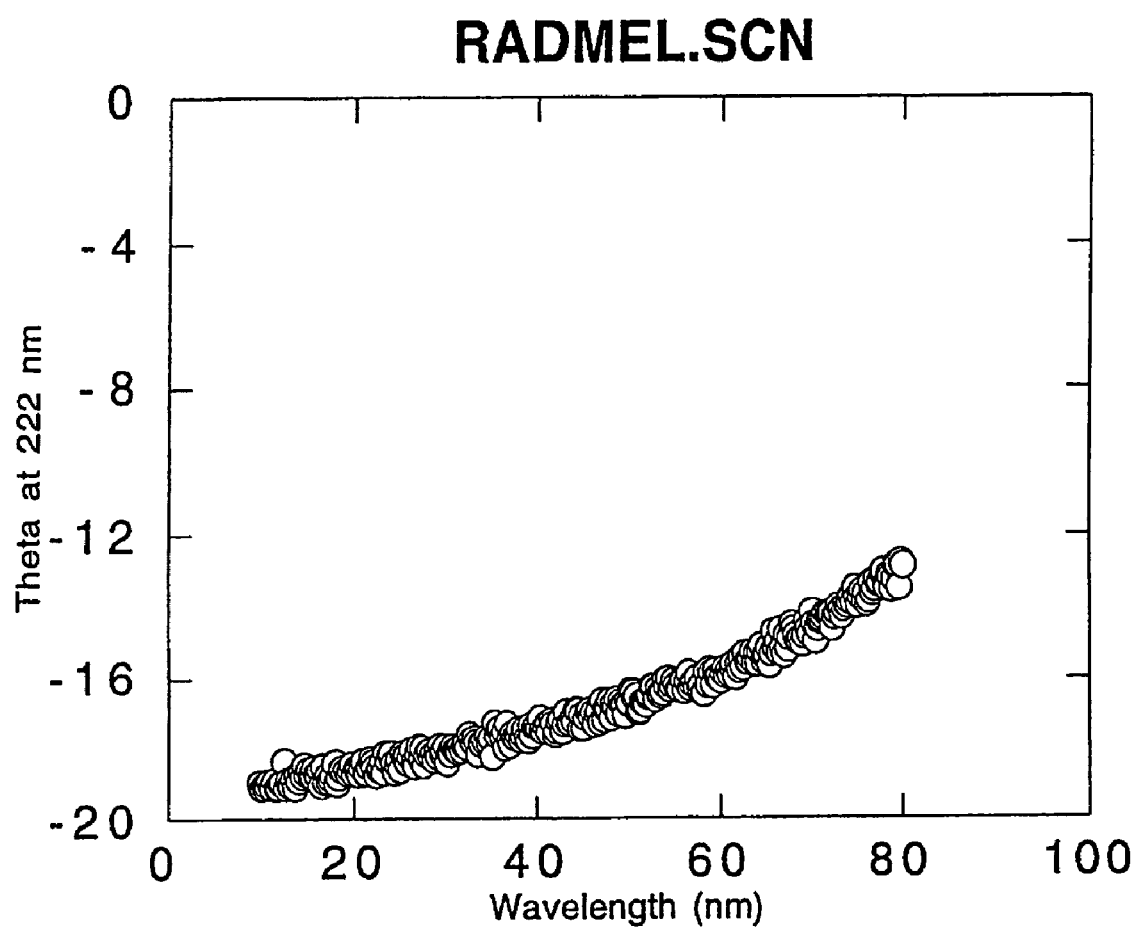
FIG. 18 is a graph showing the melt profile of Rad23 at 222 nm frequency. It is significant to note that there is no temperature dependent unfolding of the protein.

Rad23 was purified to homogeneity from bacteria and subjected to structural analysis by circular dichroism (CD-spectra). The analysis was done along with other unrelated proteins. The CD-spectra revealed that Rad23 is a typical globular protein, which is highly soluble and contains substantial α-helical character. See FIG. 17. However, when the thermal stability of the protein was analyzed, the data revealed that it did not display the cooperative melting profile typically observed for globular proteins. See FIG. 18. Indeed a melting transition was not detected even when Rad23 was heated to excess of 90° C. Further, when the protein sample was returned to 23° C. it continued to display CD-spectra consistent with a well-folded globular and soluble protein. In contrast, other proteins that were analyzed at the same time displayed the expected cooperative denaturation at 52° C., indicating that the experimental conditions and the function of the instrument were normal.

The results obtained indicate that the UbL is a cis-acting, temperature stabilizer. As described in the previous examples, UbL$^{R23}$ has been fused to β-galatosidase. Like Rad23, this fusion protein can be heated without loss of secondary structure. Additionally, exposure to high temperatures did not inactivate the enzymatic portion of the fusion protein.

This observation indicates that the UbL has broad applications in the generation of fusion proteins having enhanced thermostability.

What is claimed is:

1. A method for purification of proteasomes from cells comprising:
   a) immobilizing a ubiquitin-like (Ubl) domain of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13 to a solid support;
   b) exposing said immobilized Ubl domain to a cell lysate;
   c) binding said proteasome to said immobilized Ubl domain;
   d) eluting non-specifically bound proteins; and
   e) eluting said proteasome from said solid support, thereby purifying said proteasome from said cell lysate.

2. The method of claim 1, wherein said Ubl domain is fused with glutathione S-transferase.

3. A method for purification of a proteasome from a cell comprising exposing a recombinant ubiquitin-like (Ubl) domain of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13 which is immobilized to a solid support to a cell lysate, isolating the proteasome bound to the ubiquitin-like domain, and isolating the proteasome from the ubiquitin-like domain.

4. The method of claim 3 further comprising eluting non-specifically bound proteins from the Ubl domain.

5. The method of claim 3, wherein isolating proteasome from said Ubl domain comprises eluting said proteasome from said Ubl domain immobilized to solid support thereby purifying said proteasome from said cell lysate.

6. The method of claim 3, wherein said Ubl domain is fused with glutathione S-transferase.

* * * * *

SEQUENCE LISTING

<160> NUMBER OF SEQ ID NOS: 18

<210> SEQ ID NO 1
<211> LENGTH: 11
<212> TYPE: PRT
<213> ORGANISM: Artificial Sequence
<220> FEATURE:
<223> OTHER INFORMATION: Synthetic consensus sequence of UbL-domain
<220> FEATURE:
<221> NAME/KEY: MISC_FEATURE
<222> LOCATION: (1)..(1)
<223> OTHER INFORMATION: Xaa denotes Lys or Arg
<220> FEATURE:
<221> NAME/KEY: MISC_FEATURE
<222> LOCATION: (3)..(3)
<223> OTHER INFORMATION: Xaa denotes Leu or Ile
<220> FEATURE:
<221> NAME/KEY: MISC_FEATURE
<222> LOCATION: (4)..(4)
<223> OTHER INFORMATION: Xaa denotes a hydrophobic amino acid residue
<220> FEATURE:
<221> NAME/KEY: MISC_FEATURE
<222> LOCATION: (5)..(5)
<223> OTHER INFORMATION: Xaa denotes any amino acid residue
<220> FEATURE:
<221> NAME/KEY: MISC_FEATURE
<222> LOCATION: (8)..(8)
<223> OTHER INFORMATION: Xaa denotes any amino acid residue
<220> FEATURE:
<221> NAME/KEY: MISC_FEATURE
<222> LOCATION: (9)..(9)
<223> OTHER INFORMATION: Xaa denotes Leu or Ser
<220> FEATURE:
<221> NAME/KEY: MISC_FEATURE
<222> LOCATION: (10)..(10)
<223> OTHER INFORMATION: Xaa denotes a polar amino acid residue

<400> SEQUENCE: 1

Xaa Leu Xaa Xaa Xaa Gly Lys Xaa Xaa Xaa Asp
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic consensus sequence of UbL-domain
<220> FEATURE:
<221> NAME/KEY: MISC_FEATURE
<222> LOCATION: (1)..(1)
<223> OTHER INFORMATION: Xaa denotes Lys or Gln
<220> FEATURE:
<221> NAME/KEY: MISC_FEATURE
<222> LOCATION: (2)..(2)
<223> OTHER INFORMATION: Xaa denotes Ala or Ser
<220> FEATURE:
<221> NAME/KEY: MISC_FEATURE
<222> LOCATION: (3)..(3)
<223> OTHER INFORMATION: Xaa denotes Phe or Tyr
<220> FEATURE:
<221> NAME/KEY: MISC_FEATURE
<222> LOCATION: (4)..(4)
<223> OTHER INFORMATION: Xaa denotes Cys or Ala
<220> FEATURE:
<221> NAME/KEY: MISC_FEATURE
<222> LOCATION: (5)..(5)
<223> OTHER INFORMATION: Xaa denotes a polar amino acid residue

<400> SEQUENCE: 2

Xaa Xaa Xaa Xaa Xaa Arg Gln Gly
1               5

```
<210> SEQ ID NO 3
<211> LENGTH: 76
<212> TYPE: PRT
<213> ORGANISM: Homo sapiens

<400> SEQUENCE: 3

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 4
<211> LENGTH: 77
<212> TYPE: PRT
<213> ORGANISM: Saccharomyces cerevisiae

<400> SEQUENCE: 4

Met Ser Leu Asn Ile His Ile Lys Ser Gly Gln Asp Lys Trp Glu Val
1               5                   10                  15

Asn Val Ala Pro Glu Ser Thr Val Leu Gln Phe Lys Glu Ala Ile Asn
            20                  25                  30

Lys Ala Asn Gly Ile Pro Val Ala Asn Gln Arg Leu Ile Tyr Ser Gly
        35                  40                  45

Lys Ile Leu Lys Asp Asp Gln Thr Val Glu Ser Tyr His Ile Gln Asp
    50                  55                  60

Gly His Ser Val His Leu Val Lys Ser Gln Pro Lys Pro
65                  70                  75

<210> SEQ ID NO 5
<211> LENGTH: 77
<212> TYPE: PRT
<213> ORGANISM: Saccharomyces cerevisiae

<400> SEQUENCE: 5

Met Val Ser Leu Thr Phe Lys Asn Phe Lys Lys Glu Lys Val Pro Leu
1               5                   10                  15

Asp Leu Glu Pro Ser Asn Thr Ile Leu Glu Thr Lys Thr Lys Leu Ala
            20                  25                  30

Gln Ser Ile Ser Cys Glu Glu Ser Gln Ile Lys Leu Ile Tyr Ser Gly
        35                  40                  45

Lys Val Leu Gln Asp Ser Lys Thr Val Ser Glu Cys Gly Leu Lys Asp
    50                  55                  60

Gly Asp Gln Val Val Phe Met Val Ser Gln Lys Lys Ser
65                  70                  75

<210> SEQ ID NO 6
<211> LENGTH: 79
<212> TYPE: PRT
<213> ORGANISM: Homo sapiens

<400> SEQUENCE: 6

Met Gln Val Thr Leu Lys Thr Leu Gln Gln Gln Thr Phe Lys Ile Asp
1               5                   10                  15
```

Ile Asp Pro Glu Glu Thr Val Lys Ala Leu Lys Glu Lys Ile Glu Ser
            20                  25                  30

Glu Lys Gly Lys Asp Ala Phe Pro Val Ala Gly Gln Lys Leu Ile Tyr
        35                  40                  45

Ala Gly Lys Ile Leu Asn Asp Asp Thr Ala Leu Lys Glu Tyr Lys Ile
    50                  55                  60

Asp Glu Lys Asn Phe Val Val Met Val Thr Lys Pro Lys Ala
65                  70                  75

<210> SEQ ID NO 7
<211> LENGTH: 81
<212> TYPE: PRT
<213> ORGANISM: Homo sapiens

<400> SEQUENCE: 7

Met Ala Val Thr Ile Thr Leu Lys Thr Leu Gln Gln Gln Thr Phe Lys
1               5                   10                  15

Ile Arg Met Glu Pro Asp Glu Thr Val Lys Val Leu Lys Glu Lys Ile
            20                  25                  30

Glu Ala Glu Lys Gly Arg Asp Ala Phe Pro Val Ala Gly Gln Lys Leu
        35                  40                  45

Ile Tyr Ala Gly Lys Ile Leu Ser Asp Asp Val Pro Ile Arg Asp Tyr
    50                  55                  60

Arg Ile Asp Glu Lys Asn Phe Val Val Val Met Val Thr Lys Thr Lys
65                  70                  75                  80

Ala

<210> SEQ ID NO 8
<211> LENGTH: 83
<212> TYPE: PRT
<213> ORGANISM: Saccharomyces cerevisiae

<400> SEQUENCE: 8

Ala Val His Leu Thr Leu Lys Lys Ile Gln Ala Pro Lys Phe Ser Ile
1               5                   10                  15

Glu His Asp Phe Ser Pro Ser Asp Thr Ile Leu Gln Ile Lys Gln His
            20                  25                  30

Leu Ile Ser Glu Glu Lys Ala Ser His Ile Ser Glu Ile Lys Leu Leu
        35                  40                  45

Leu Lys Gly Lys Val Leu His Asp Asn Leu Phe Leu Ser Asp Leu Lys
    50                  55                  60

Val Thr Pro Ala Asn Ser Thr Ile Thr Val Met Ile Lys Pro Asn Pro
65                  70                  75                  80

Thr Ile Ser

<210> SEQ ID NO 9
<211> LENGTH: 76
<212> TYPE: PRT
<213> ORGANISM: Saccharomyces cerevisiae

<400> SEQUENCE: 9

Met Ile Val Lys Val Lys Thr Leu Thr Gly Lys Glu Ile Ser Val Glu
1               5                   10                  15

Leu Lys Glu Ser Asp Leu Val Tyr His Ile Lys Glu Leu Leu Glu Glu
            20                  25                  30

Lys Glu Gly Ile Pro Pro Ser Gln Gln Arg Leu Ile Phe Gln Gly Lys
        35                  40                  45

His Ser Asp Asp Lys Leu Thr Val Thr Asp Ala His Leu Val Glu Gly
            50                  55                  60

Met Gln Leu Lys Leu Val Leu Thr Leu Arg Gly Gly
 65                  70                  75

<210> SEQ ID NO 10
<211> LENGTH: 101
<212> TYPE: PRT
<213> ORGANISM: Homo sapiens

<400> SEQUENCE: 10

Met Ser Asp Gln Glu Ala Lys Pro Ser Thr Glu Asp Leu Gly Asp Lys
 1               5                  10                  15

Lys Glu Gly Glu Tyr Ile Lys Leu Lys Val Ile Gly Gln Asp Ser Ser
                20                  25                  30

Glu Ile His Phe Lys Val Lys Met Thr Thr His Leu Lys Lys Leu Lys
            35                  40                  45

Glu Ser Tyr Cys Gln Arg Gln Gly Val Pro Met Asn Ser Leu Arg Phe
 50                  55                  60

Leu Phe Glu Gly Gln Arg Ile Ala Asp Asn His Thr Pro Lys Glu Leu
 65                  70                  75                  80

Gly Met Glu Glu Glu Asp Val Ile Glu Val Tyr Gln Glu Gln Thr Gly
                85                  90                  95

Gly His Ser Thr Val
            100

<210> SEQ ID NO 11
<211> LENGTH: 95
<212> TYPE: PRT
<213> ORGANISM: Saccharomyces cerevisiae

<400> SEQUENCE: 11

Met Ala Asp Glu Lys Pro Lys Glu Gly Val Lys Thr Glu Asn Asn Asp
 1               5                  10                  15

His Ile Asn Leu Lys Val Ala Gly Gln Asp Gly Ser Val Val Gln Phe
                20                  25                  30

Lys Ile Lys Arg His Thr Pro Leu Ser Lys Leu Met Lys Ala Tyr Cys
            35                  40                  45

Glu Arg Gln Gly Leu Ser Met Arg Gln Ile Arg Phe Arg Phe Asp Gly
 50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                85                  90                  95

<210> SEQ ID NO 12
<211> LENGTH: 95
<212> TYPE: PRT
<213> ORGANISM: Saccharomyces cerevisiae

<400> SEQUENCE: 12

Met Ser Glu Glu Lys Pro Lys Glu Gly Val Lys Thr Glu Asn Asp His
 1               5                  10                  15

Ile Asn Leu Lys Val Ala Gly Gln Asp Gly Ser Val Val Gln Phe Lys
                20                  25                  30

Ile Lys Arg His Thr Ser Leu Ser Lys Leu Met Lys Ala Tyr Cys Glu
            35                  40                  45

Arg Gln Gly Leu Ser Met Arg Gln Ile Arg Phe Arg Phe Asp Gly Gln

```
                50                  55                  60
Pro Ile Asn Glu Thr Asp Thr Pro Ala Gln Leu Arg Met Glu Asp Glu
 65                  70                  75                  80

Asp Thr Ile Asp Val Phe Gln Gln Gln Thr Gly Gly Val Pro Glu
                 85                  90                  95

<210> SEQ ID NO 13
<211> LENGTH: 100
<212> TYPE: PRT
<213> ORGANISM: Saccharomyces cerevisiae

<400> SEQUENCE: 13

Met Ser Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
                35                  40                  45

Met Glu Ala Phe Ala Lys Arg Gln Gly Lys Glu Met Asp Ser Leu Arg
 50                  55                  60

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly Ala Thr
            100

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Tyr Pro Tyr Asp Val Pro Asp Tyr Ala
 1               5

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
gcgaattcat ggttagctta acc                                         23

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
gcggtacccg tcggcatgat cgctg                                       25

<210> SEQ ID NO 17
<211> LENGTH: 32
<212> TYPE: DNA
<213> ORGANISM: Artificial Sequence
```

```
<220> FEATURE:
<223> OTHER INFORMATION: Synthetic primer

<400> SEQUENCE: 17
gcgaattcat gacgaagacc aaactaacag aa                           32

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
gaagataccc caccaaac                                           18
```